(12) United States Patent
Liu

(10) Patent No.: US 11,052,346 B2
(45) Date of Patent: Jul. 6, 2021

(54) DEVICE AND METHOD FOR SEPARATION OF WATER FROM MIXTURES

(71) Applicant: Molecule Works Inc., Richland, WA (US)

(72) Inventor: Wei Liu, Richland, WA (US)

(73) Assignee: Molecule Works Inc., Richland, WA (US)

( * ) Notice: Subject to any disclaimer, the term of this patent is extended or adjusted under 35 U.S.C. 154(b) by 299 days.

(21) Appl. No.: 16/235,087

(22) Filed: Dec. 28, 2018

(65) Prior Publication Data
US 2019/0358580 A1    Nov. 28, 2019

Related U.S. Application Data

(60) Provisional application No. 62/675,289, filed on May 23, 2018.

(51) Int. Cl.
| | |
|---|---|
| *B01D 53/22* | (2006.01) |
| *B01D 53/26* | (2006.01) |
| *B01D 69/10* | (2006.01) |
| *B01D 63/08* | (2006.01) |
| *B01D 71/02* | (2006.01) |

(52) U.S. Cl.
CPC ......... *B01D 53/228* (2013.01); *B01D 53/268* (2013.01); *B01D 63/082* (2013.01); *B01D 69/10* (2013.01); *B01D 71/028* (2013.01); *B01D 2053/222* (2013.01)

(58) Field of Classification Search
CPC .... B01D 69/10; B01D 63/082; B01D 53/228; B01D 53/268; B01D 2053/222; B01D 71/028
See application file for complete search history.

(56) References Cited

U.S. PATENT DOCUMENTS

| | | | | |
|---|---|---|---|---|
| 2,379,792 A | * | 7/1945 | Donlan | C09K 5/20 252/78.5 |
| 3,129,816 A | * | 4/1964 | Bond | C09J 7/245 428/356 |

(Continued)

OTHER PUBLICATIONS

S. Wee, et al., "Membrane separation process-pervaporation through zeolite membrane" Sep. Purif. Technol., 63, (2008) 500.

(Continued)

*Primary Examiner* — Anthony R Shumate
(74) *Attorney, Agent, or Firm* — The Marbury Law Group, PLLC

(57) ABSTRACT

A membrane device and separation process are presented to enable removal of water from water-containing mixtures at high throughput and high energy efficiency. The membrane device is made of thin $H_2O$-selective molecular sieve membrane sheets with small feed channels and small permeate channels. The thin membrane sheet provides $H_2O$-molecular specificity and allows $H_2O$ molecule to permeate through while blocking the other molecules. The membrane device provides large membrane area per unit volume and reduces mass transfer and flow resistance. Water is removed from the mixture by flowing the water-containing mixture through the feed channels of the device at a pressure above atmospheric pressure and removing the permeated water vapor from the permeate channels in the device under vacuum.

17 Claims, 16 Drawing Sheets

(56) References Cited

U.S. PATENT DOCUMENTS

| | | | |
|---|---|---|---|
| 6,420,004 B1* | 7/2002 | Veyrat | C08J 7/0427 |
| | | | 428/36.6 |
| 7,399,892 B2 | 7/2008 | Rix et al. | |
| 7,732,173 B2 | 6/2010 | Mairal et al. | |
| 2002/0192742 A1* | 12/2002 | Ushiyama | C12M 25/14 |
| | | | 435/34 |
| 2006/0117955 A1* | 6/2006 | Cranford | B01D 53/228 |
| | | | 96/14 |
| 2008/0207959 A1 | 8/2008 | Plante et al. | |
| 2009/0215139 A1* | 8/2009 | Datta | C12P 7/08 |
| | | | 435/162 |
| 2011/0152584 A1* | 6/2011 | Pasanen | C07C 29/76 |
| | | | 568/916 |
| 2015/0053607 A1* | 2/2015 | Liu | B01D 71/68 |
| | | | 210/500.3 |
| 2015/0328122 A1* | 11/2015 | Blackburn | A61K 8/416 |
| | | | 132/203 |
| 2015/0343388 A1* | 12/2015 | Hester | B01D 71/68 |
| | | | 210/322 |
| 2016/0195641 A1* | 7/2016 | Yang | B32B 27/08 |
| | | | 428/339 |
| 2016/0293338 A1* | 10/2016 | Tanaka | H01G 9/02 |
| 2018/0111153 A1* | 4/2018 | Tanikawa | B05D 3/007 |
| 2018/0111837 A1* | 4/2018 | Tsapatsis | B01J 29/40 |
| 2021/0008506 A1* | 1/2021 | Puspasari | B01D 61/362 |

OTHER PUBLICATIONS

Y. Morigami, et al. "The first large-scale pervaporation plant using tubular-type module with zeolite NaA membrane" Sep. Purif. Technol., 25, (2001) 251.

W. Liu, et al., "Preparation of Robust, Thin Zeolite Membrane Sheet for Molecular Separation" Ind. Eng. Chem. Res., 50, (20) (2011) 11677-11689.

S. Augustin, et al. Desalination, 146, (2002) 23-28.

J. R. Kwiatowski, et al., "Modeling the process and costs of fuel ethanol production by the core dry-grind process" Ind. Crop. Prod., 23, (2006) 288.

* cited by examiner

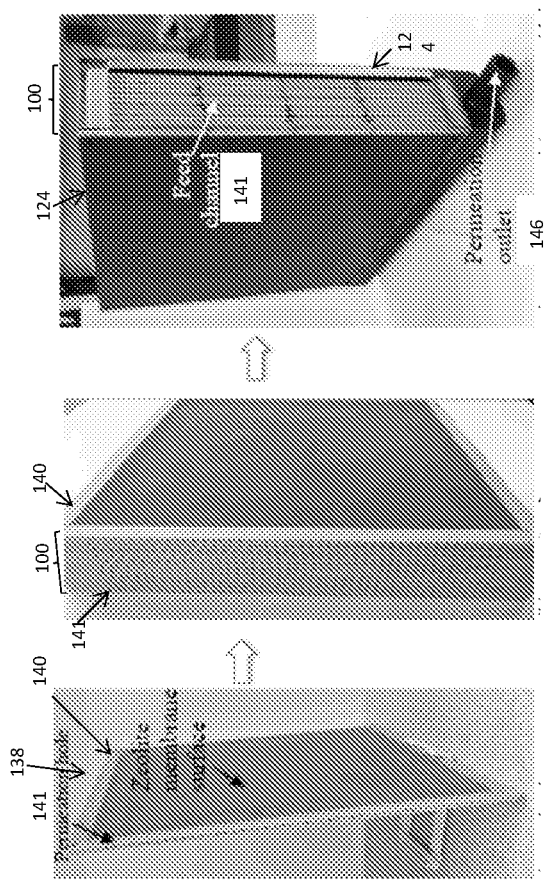
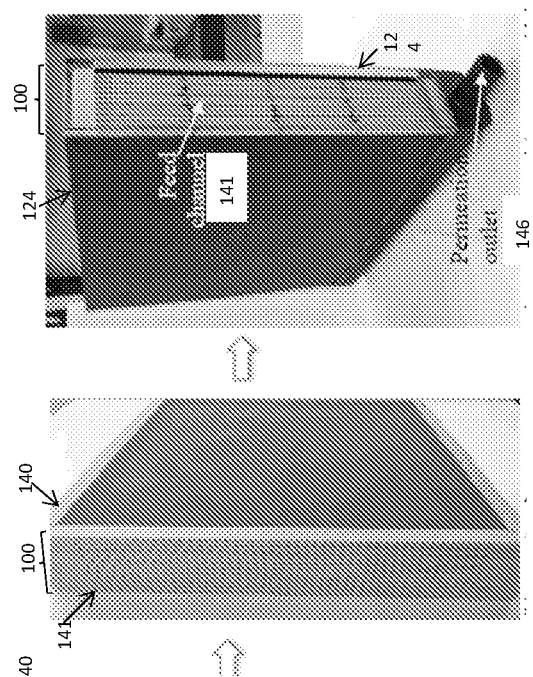
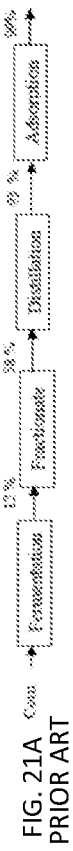
FIG. 20A
FIG. 20B
FIG. 20C
FIG. 21A
PRIOR ART
FIG. 21B
FIG. 21C

DEVICE AND METHOD FOR SEPARATION OF WATER FROM MIXTURES

CROSS REFERENCE TO RELATED PATENT APPLICATION

This application claims the benefit of U.S. Provisional Application No. 62/675,289, filed May 23, 2018, hereby incorporated herein by reference in its entirety.

FIELD OF THE INVENTION

The present invention is directed to fluid separation devices and methods.

BACKGROUND

Water removal from water-containing mixtures, particularly from water-miscible hydrocarbon mixtures, is a major problem in industries. Selective adsorption or absorption is effective if water concentration in the mixture is small, such as less than 1 wt. %. If the water concentration is significant (such as greater than 1 wt. %), the equipment size and the regeneration energy consumption increase dramatically so that the adsorption or absorption can become costly. Distillation is a commonly-used bulk separation process in the industry. Distillation consumes great amounts of thermal energy if components in the mixture have close boiling points. Distillation becomes infeasible if the boiling points are the same or an azeotropic mixture is formed. At the azeotropic point, the vapor-phase and liquid-phase have the same composition so that no molecular separation can be realized. As listed in table 1, water often forms an azeotropic mixture with hydrocarbons.

Among all the water-hydrocarbon or water-alcohol mixtures, separation of ethanol-water mixtures is of particular interest because anhydrous ethanol fuel is used worldwide. Ethanol is blended into gasoline in many countries. For a hydrocarbon fuel blend, ethanol must be dried sufficiently (e.g., 99 wt. % ethanol). Ethanol is typically produced as a water mixture. Fermentation of corn and sugar cane produces a water broth containing about 10-13 wt. % ethanol. Ethanol content in the fermentation broth of cellulosic feedstock is even much lower, Catalytic conversion of syngas ($4H_2 + 2CO \rightarrow C_2H_5OH + H_2O$) also produces an ethanol-water mixture. Water content is 50 mol % or 28 wt. % even with stoichiometric conversion. Water and ethanol form an azeotropic mixture at 95.5 wt. % ethanol. In separation of water-ethanol mixtures, ethanol is first enriched by distillation to about 93-94 wt. %, slightly below the azeotropic point, and the remaining water is scrubbed on a water-selective zeolite adsorbent to reach 99% purity. The saturated adsorbent is regenerated by heating at high temperatures (around 150° C.). The separation process is energy and capital intensive.

Membrane separation has been long sought for efficient separation of water-hydrocarbon mixtures, including ethanol-water. Membrane separation is a steady-state, continuous process, and does not involve constant heating and cooling (i.e. temperature swing) as is needed in adsorption and distillation processes. Membrane separation is based on molecular selectivity of the membrane and is not limited by formation of an azeotropic point. A variety of membrane materials have been studied. The porous ceramic tube-supported zeolite membrane was reported to provide very high flux and water/ethanol selectivity relative to polymeric membranes. However, a very large number of such membrane tubes is needed to conduct industrial-scale separations such as in ethanol fuel plants. For example, about 70,000 of 1 m-long and 1 cm-diameter membrane tubes are needed for dewatering of 55 wt. % ethanol in an ethanol fuel plant of 40 million gallon/year capacity (about 120,000 ton/yearn. It leas been very challenging technically and economically to assemble such large number of ceramic-based membrane tubes into separation modules, because the ceramic tubes are fragile. Thus, membrane separation has not been widely used for large-scale industrial de-watering processes.

TABLE 1

Boiling point of binary mixtures of water with hydrocarbons

| Name of 2nd Component | Wt. % in azeotropic mixture | b.p. of azeotropic mixture (° C.) | b.p. of 2nd Component. (° C.) |
| --- | --- | --- | --- |
| ethanol | 95.5 | 78.1 | 78.4 |
| methanol |  | No azeotrope | 64.7 |
| n-propanol | 71.7 | 87.7 | 97.2 |
| iso-propanol | 87.7 | 80.4 | 82.5 |
| n-butanol | 55.5 | 92.4 | 117.8 |
| sec-butanol | 67.9 | 88.5 | 99.5 |
| iso-butanol | 70 | 90 | 108 |
| tert-butanol | 88.3 | 79.9 | 82.8 |
| allyl alcohol | 72.9 | 88.2 | 97 |
| benzyl alcohol | 9 | 99.9 | 205.2 |
| furfuryl alcohol | 20 | 98.5 | 169.4 |
| cyclohexanol | 20 | 97.8 | 161.1 |
| benzyl alcohol | 9 | 99.9 | 205.4 |
| acetone |  | No azeotrope | 56.5 |
| methyl ethyl ketone | 89 | 73.5 | 79.6 |
| acetonitrile | 83.7 | 76.5 | 82 |

The compact and high throughput membrane separation method described herein provides a solution to the efficient separation of water-hydrocarbon mixtures at industrial scale.

SUMMARY

The embodiments herein describe a mini-channel separation device comprising thin $H_2O$-selective molecular sieve membrane sheets. As illustrated in FIG. 1, the thin membrane sheets 102 are stacked to form a stack 100 in which the membrane sheets 102 are arranged face-to-face to form mini-flow feed channels 114 for water-hydrocarbon mixtures (i.e. feed 101) to pass through, while the other side of the membrane sheet 102 is supported by a backing structure 110 comprising mini-channels for the permeated water vapor (i.e. permeate channels 112) to flow out. A cushion 108 may be placed between the membrane sheet 102 and the backing structure 110.

In an embodiment illustrated in FIG. 1B, the thin membrane sheet 102 comprises a water-selective molecular sieve layer 120 grown on a thin porous support sheet 122. The molecular sieve layer 120 thickness is preferably less than 20 μm, more preferably less than 10 μm. The thin porous support sheet 122 may be made of metallic material and have a thickness preferably less than 200 μm, preferably less than 100 μm. The surface of the support sheet 122 for growing the molecular sieve membrane 120 is substantially free, such as less than less than 10% of pores above 5 μm in diameter.

The two membrane sheets 102 in the feed channel 114 are spaced at a height in the range of 0.3 to 3.0 mm. The channel spacing is small enough to increase packing density of the membrane sheets 102 per unit volume and to reduce concentration polarization of the feed mixture under the separation conditions. The feed channel spacing is large enough to reduce the pressure drop for the feed to pass through the feed channel 114.

In an embodiment, the backing structure 110 comprises permeate flow channels 112 having a hydraulic diameter in the range of 1 to 5 mm with an open frontal fraction of 0.4 to 0.9. The open frontal fraction is defined as ratio of the cross-sectional area for the permeate to flow to the total cross-sectional area. The hydraulic diameter is large enough for the permeated water vapor 118 to transport out of the membrane device at minimal pressure drop. The hydraulic diameter is preferably small enough to enhance the backing structure strength and reduce volume of the device. The permeate channels 112 are preferably straight to reduce the pressure drop. In an embodiment, the backing structure 110 is made of durable metallic material. The thickness of the cushion layer 108 between the membrane sheet 102 and the backing structure 110 is about 0 to about 0.5 mm.

An embodiment includes a process for dewatering of a water-hydrocarbon mixture 101 comprising i) passing the mixture through an array of feed channels 114 in a mini-channel separation device with a predetermined space velocity, temperature, and pressure; ii) transporting water molecules from the water-hydrocarbon mixture 101 across the membrane sheet 102 in the mini-channel separation device, and iii) removing the permeated water vapor 118 through the permeate channels 112 in the separation device at a predetermined pressure.

In an embodiment, the water-hydrocarbon mixture 101 contains less than 50 wt. % water. The feed temperature is in the range of 60 to 200° C. and pressure is preferably above atmospheric pressure, preferably 1-5 bars. The fluid/membrane contact can be characterized by the liquid-hourly space velocity (LHSV) if the feed is in liquid phase or gas-hourly space velocity (GHSV) if the feed is in vapor phase. The LHSV and the GHSV can be calculated as follows:

$$LHSV = \frac{Q_{f,liq}}{V_{F,m}}, \quad (1)$$

$$GHSV = \frac{Q_{f,gas}}{V_{F,m}} \quad (2)$$

Where $Q_{f,liq}$=flow rate of feed in liquid phase, liter/h; $Q_{f,gas}$=flow rate of feed in vapor phase, liter/h; $V_{F,m}$=volume of membrane channels that are exposed to the feed, liter.

The higher the space velocity, the less residence time the fluid has inside the feed channel. For practical applications, LHSV is preferably above 10 l/h and GHSV is preferably above 1,000 l/h.

Feed flow velocity is another operating parameter for practical application. It can be calculated by use of the following equation:

$$U = \frac{Q_f}{SA_{F,m}} \quad (3)$$

Where $Q_f$=feed flow rate, cc/s; $SA_{F,m}$=cross-flow area of membrane channels, cm$^2$, U=superficial linear velocity, cm/s.

To minimize concentration polarization in the feed channel, i.e., the concentration difference of water between the bulk flow and membrane surface, high superficial linear velocity and small channel size are preferred. However, the pressure drop increases with superficial linear velocity and decreasing channel size. In an embodiment, the superficial linear velocity is preferably above 10 cm/s. The pressure drop for the feed flow through the separation device is preferably less than 1 bar.

The permeate pressure is preferably lower than the feed pressure and is preferably below 1 bar, more preferably below 20 kPa.

BRIEF DESCRIPTION OF THE DRAWINGS

FIG. 10A 10 wt. % water in ethanol, FIG. 10B separation temperature equals 75° C.

Figure 14:
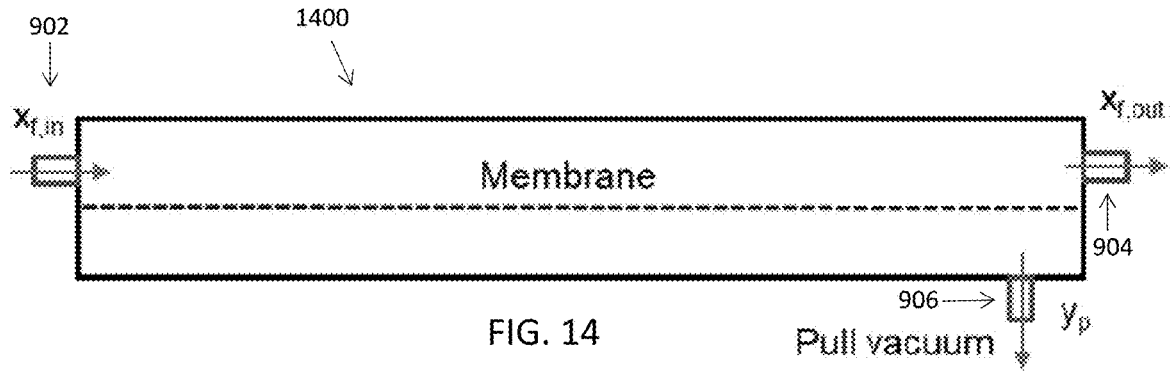

FIG. 14 is a schematic illustration of an integral mini-channel test cell according to an embodiment.

Figure 15A:
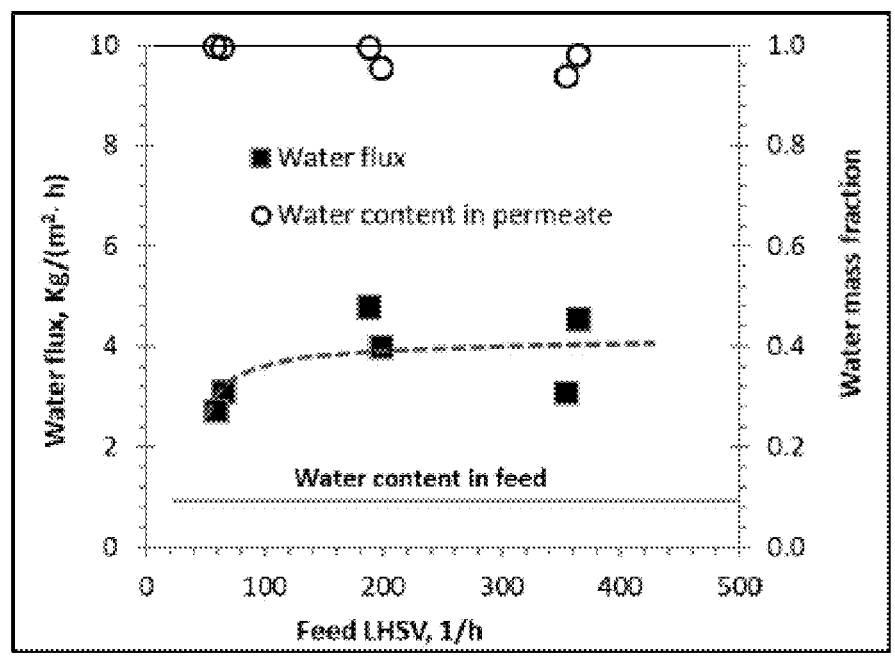
Figure 15B:
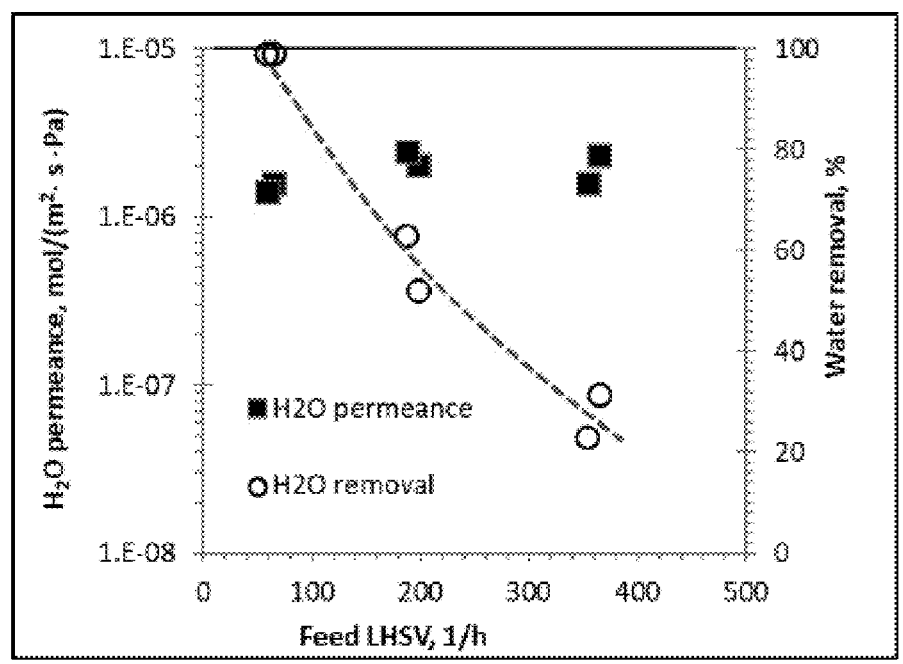

FIGS. 15A and 15B are plots illustrating the performance of a mini-channel test cell at different LHSV (feed composition: 10 wt. % water (=22 mol %); feed pressure=120±14 kPa; Feed $U_f$=36-180 cm/s; Separation temperature: 89.4±3.3° C.; permeate pressure: 0.13 KPa) according to an embodiment. FIG. 15A illustrates the variation of water flux and permeate water content with LHSV; FIG. 15B illustrates the variation of $H_2O$ permeance and one-pass water removal with LHSV.

Figure 16A:
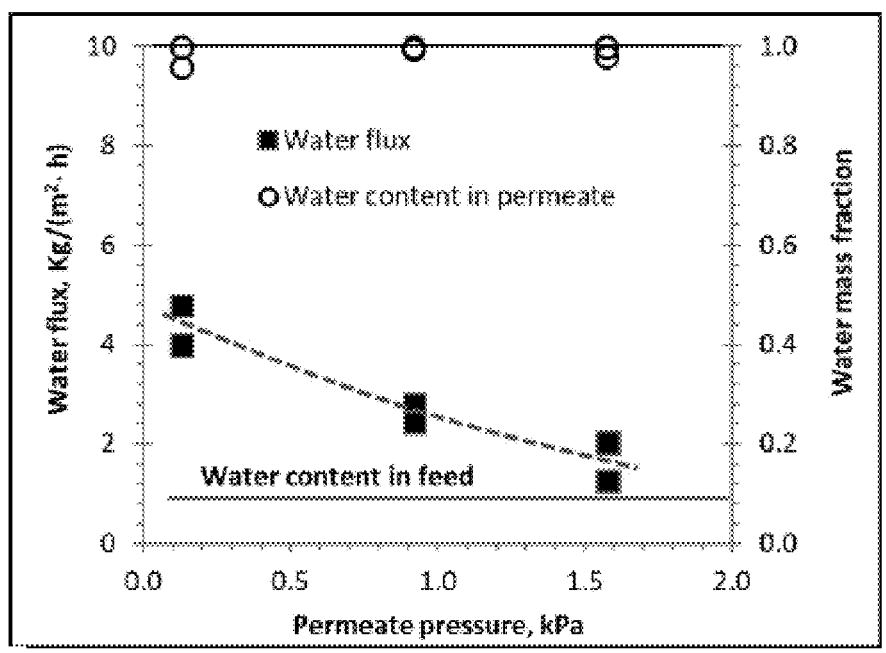
Figure 16B:
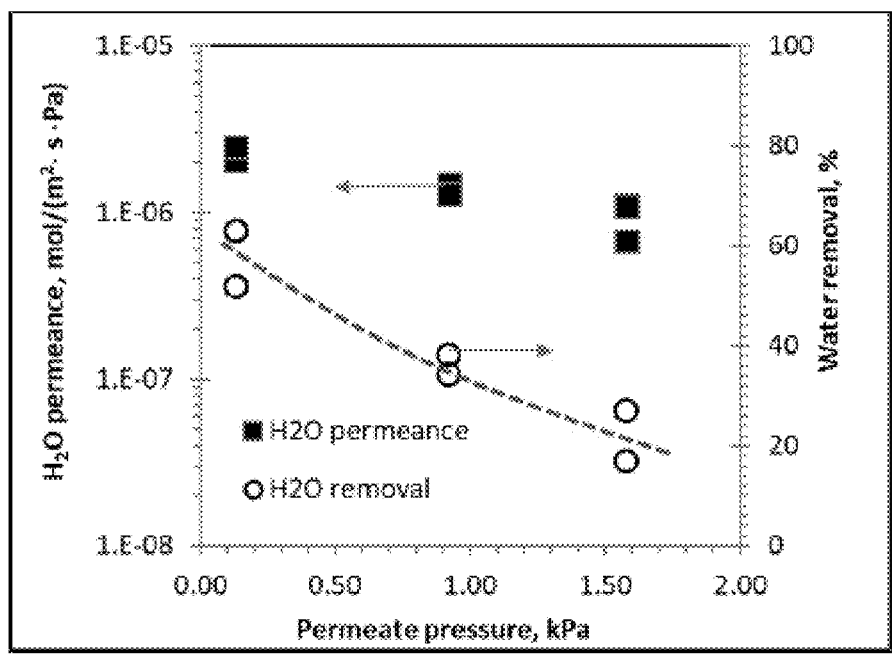

FIGS. 16A and 16B are plots illustrating the performance of a mini-channel test cell at different permeate pressure (feed composition: 735 g of ethanol/liter or 10 wt. % water (=22 mol %); feed pressure=116+/−1.2 kPa; Feed LHSV=185 l/h, $U_f$=108 cm/s; separation temperature: 89.7+/−1.9° C.) according to an embodiment, FIG. 16A illustrates the variation of water flux and permeate water content with permeate pressure; FIG. 16B illustrates the variation of $H_2O$ permeance and one-pass water removal with permeate pressure.

Figure 17A:
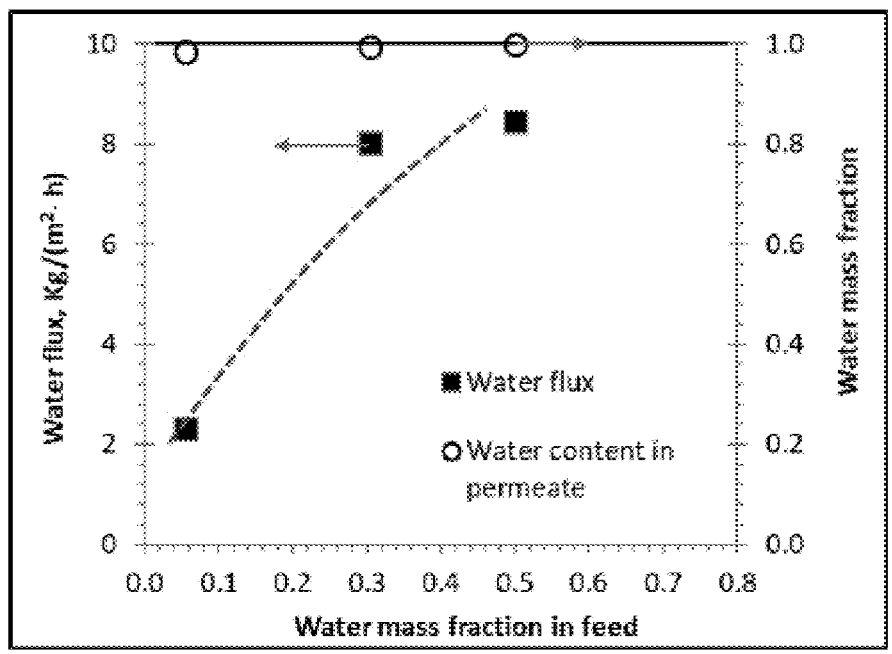
Figure 17B:
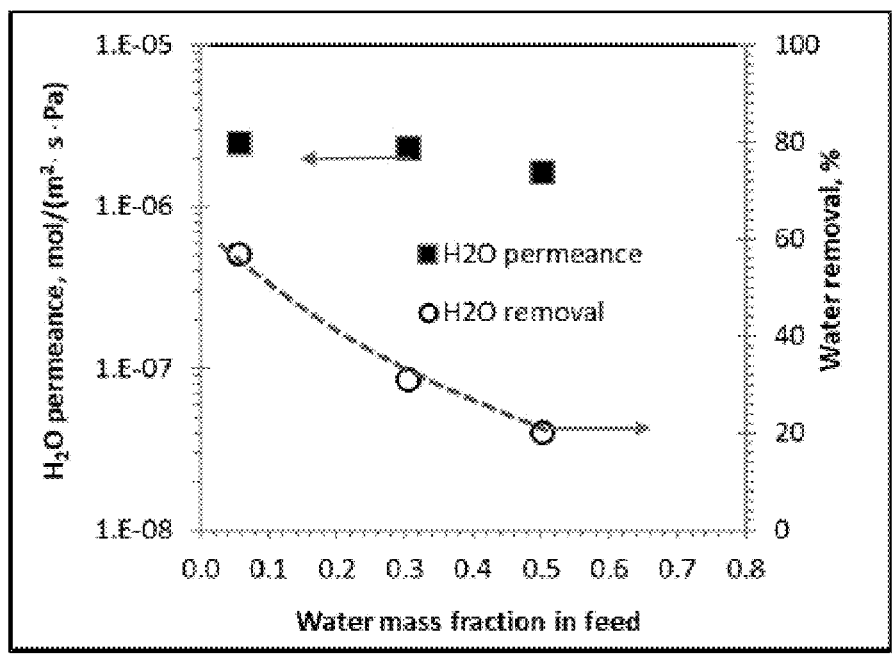

FIGS. 17A and 17B are plots illustrating the performance of a mini-channel test cell with different water content in the feed (feed pressure=118 kPa; Feed LHSV=185 l/h, Separation temperature: 91.4° C.; permeate pressure=1.9 kPa) according to an embodiment. FIG. 17A illustrates the variation of water flux and permeate water content; FIG. 17B illustrates the variation of $H_2O$ permeance and one-pass water removal.

Figure 18A:
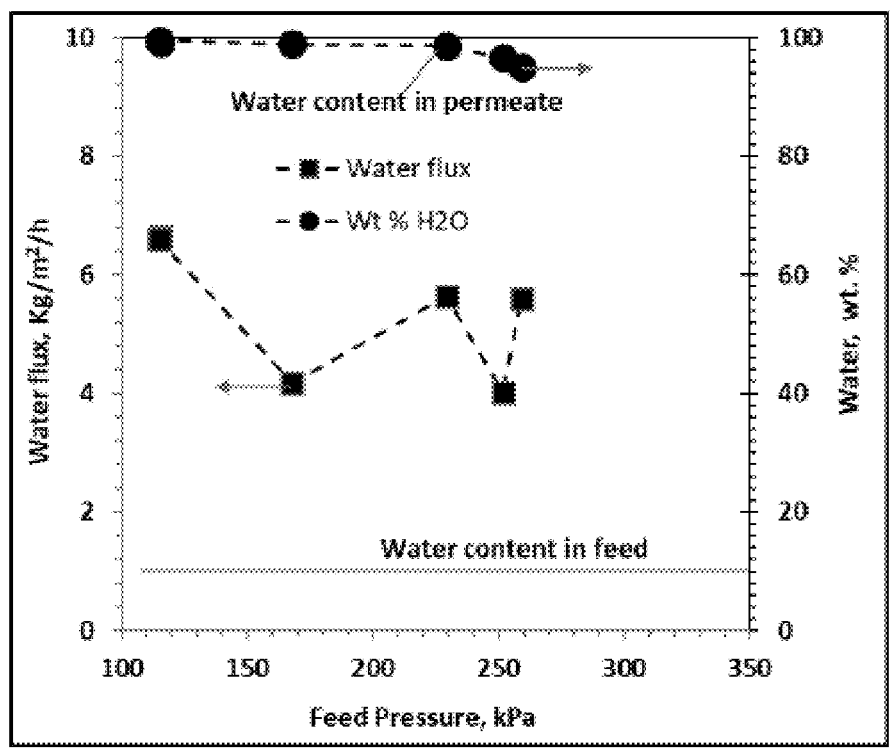
Figure 18B:
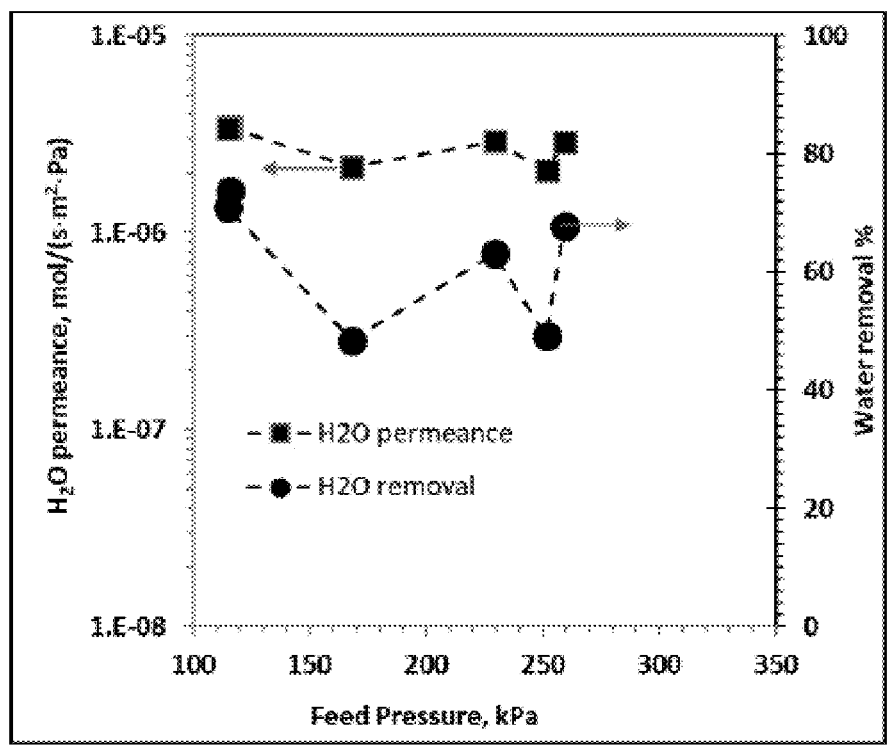

FIGS. 18A and 18B are plots illustrating the performance of a mini-channel test cell at different feed pressure (feed composition: 735 g of ethanol/liter or 10 wt. % water (=22 mol %); feed LHSV=180-165 l/h, $U_f$=260-105 cm/s; Separation temperature: 89.3+/−1.5° C.; permeate pressure: 0.1 KPa) according to an embodiment. FIG. 18A illustrates the variation of water flux and permeate water content; FIG. 18B illustrates the variation of $H_2O$ permeance and one-pass water removal.

Figure 19A:
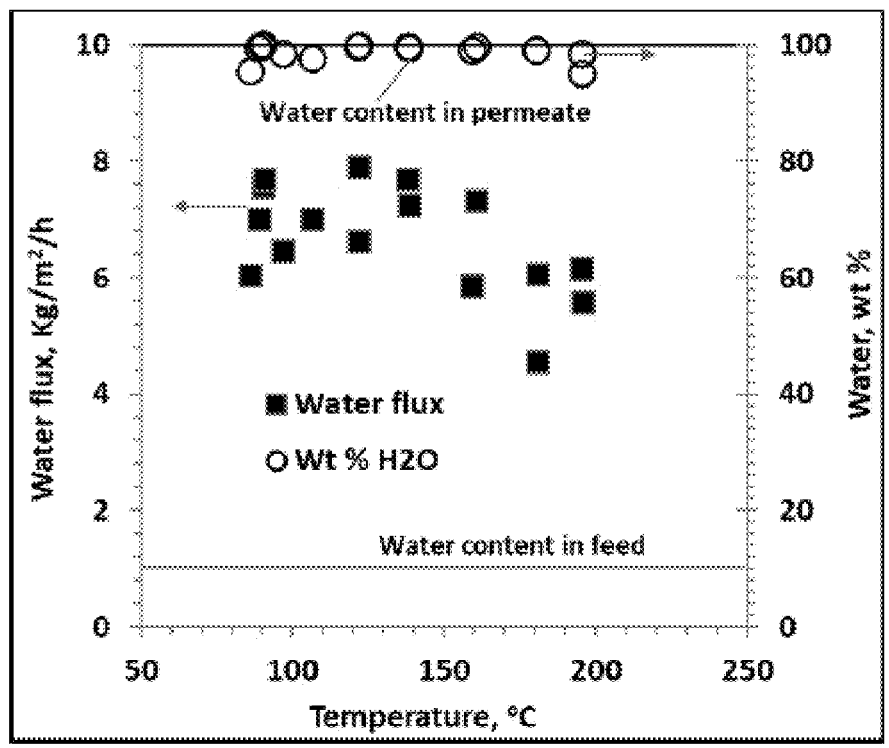
Figure 19B:
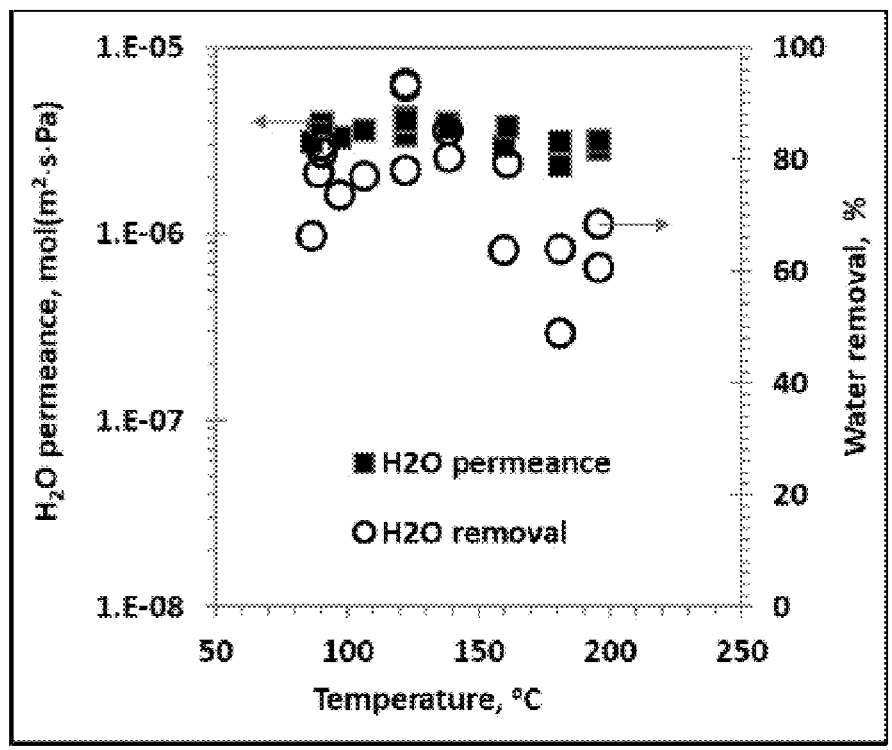

FIGS. 19A and 19B are plots illustrating the performance of a mini-channel test cell at different temperature (feed composition: 735 g of ethanol/liter or 10 wt. % water (=22 mol %); feed LHSV=180-165 l/h, $U_f$=260-105 cm/s; feed pressure=168+/−46 kPa; permeate pressure: 0.13 KPa). FIG. 18A illustrates the variation of water flux and permeate water content; FIG. 18B illustrates the variation of $H_2O$ permeance and one-pass water removal.

FIGS. 20A-20C illustrate an embodiment of a mini-channel membrane stack assembly including: FIG. 20A, a single cassette, FIG. 20B, a stack of cassettes and FIG. 20C, a stack inserted into a manifold.

FIGS. 21A-21C illustrate process schemes for ethanol/water separation in dry mill-based corn ethanol plants (numbers are wt % ethanol process stream) according to an embodiment in which FIG. 21A illustrates a conventional water-ethanol separation process, FIG. 21B illustrates replacing distillation with membrane separation and FIG. 21C illustrates replacing distillation and absorption with membrane separation.

Figure 10A:
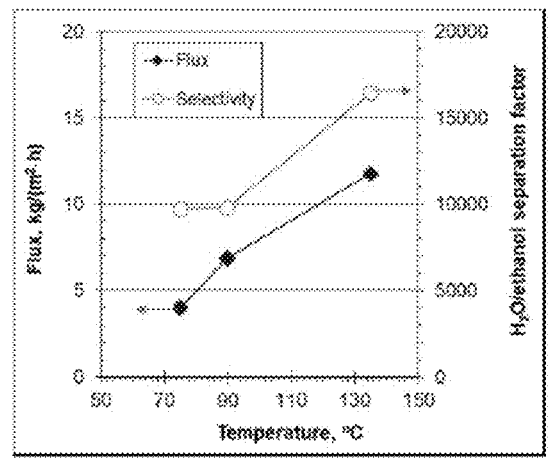
FIGS. 10A and 10B are plots illustrating the performance characteristics of a membrane for ethanol-water separation (feed pressure equals 105 kPa, permeate pressure equals 0.1 kPa) according to an embodiment.
Figure 10B:
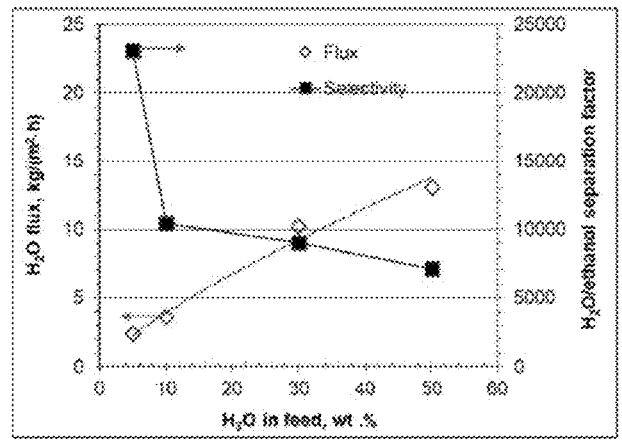
Figure 22A:
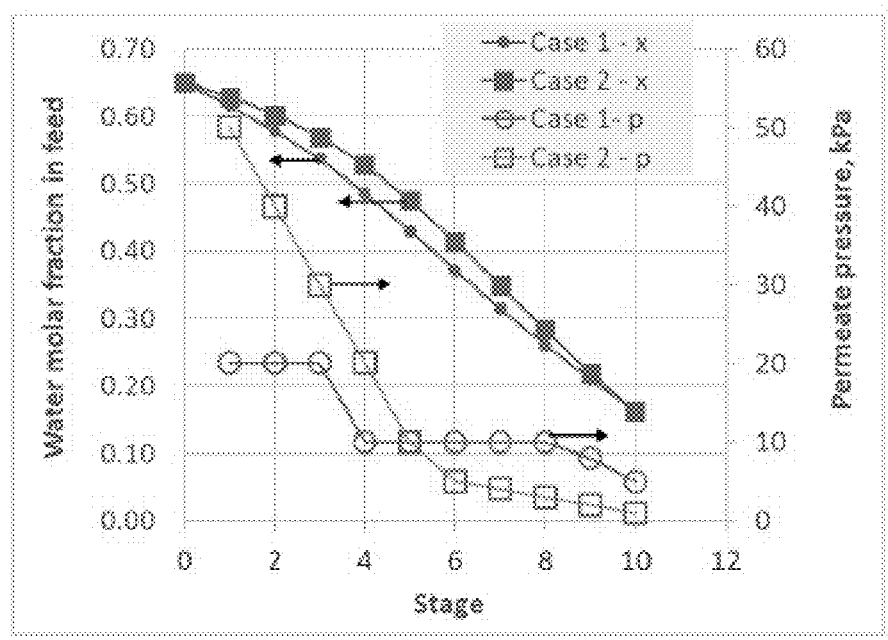
Figure 22B:
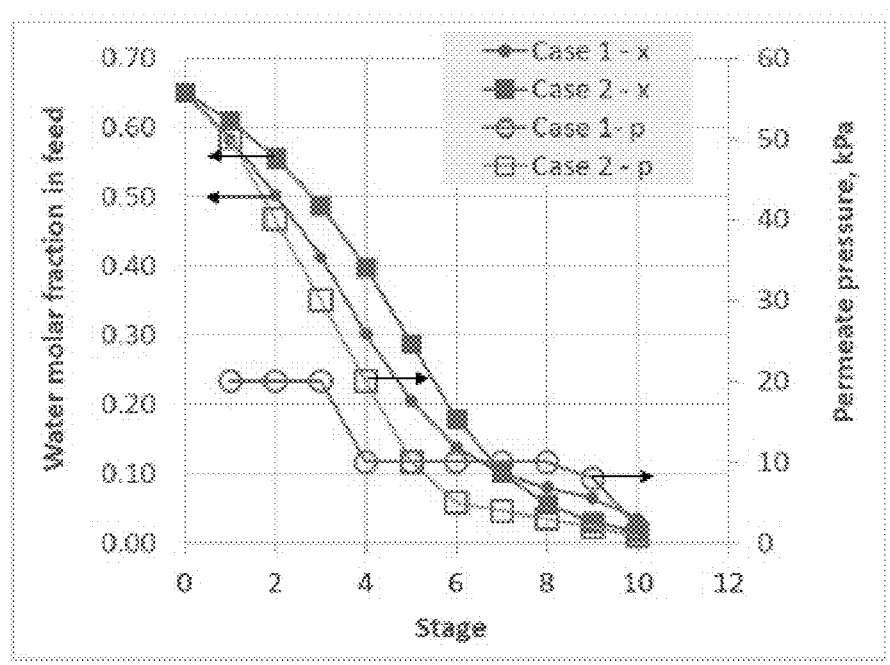

FIGS. 22A and 22B are plots illustrating dewatering of a commercial-scale ethanol plant (feed conditions: vapor phase, 373K, 180 kPa, 42.1 wt. % water in ethanol (65 mol. % water); membrane permeance=2.0E-6 mol/(m² s Pa); ethanol flow rate=350 kmol/h (28,800 ton/year)); FIG. 22A 10 stages of 160 m² membrane device (1600 m² total), FIG. 22B Two parallel 10 stages of 160 m² membrane device (3200 m² total)

DETAILED DESCRIPTION

The following description includes embodiments of the present invention. The invention is not limited to the illustrated embodiments but that the invention also includes a variety of modifications and embodiments thereto. Therefore, the present description should be illustrative and not limiting. While the invention is amenable to various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims.

Figure 1A:
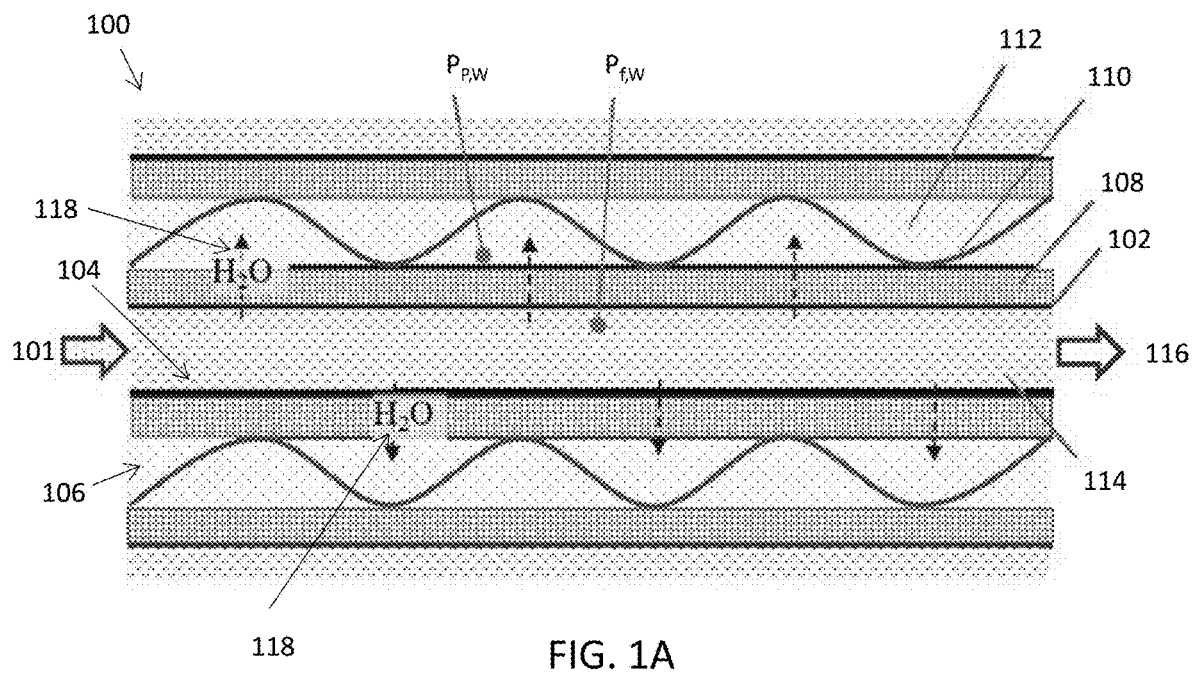
FIG. 1A is a schematic illustration of a device comprising H$_2$O-selective membrane sheets for separation of H$_2$O-hydrocarbon mixtures according to an embodiment.
Figure 1B:
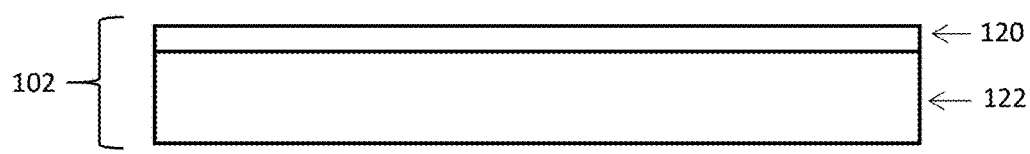
FIG. 1B is a schematic illustration of a membrane sheet according to an embodiment.

FIG. 1 shows basic features of an embodiment of a mini-channel membrane separation device 100 for dewatering of water-hydrocarbon mixtures 101 at high productivity and high efficiency, which includes one or more thin membrane sheets 102, mini-feed channels 114 and mini-permeate channels 112. The thin $H_2O$-selective membrane sheet 102 in the device 100 provides the function of separating water molecules from the mixture at sufficiently high permeance and selectivity. For most practical applications, the $H_2O$ permeance is preferably above 1.0E-6 mol/mol/m²/s and the separation factor of $H_2O$ to the other molecules is preferably above 2, preferably above 10. The permeance and separation factor are defined by the following equation:

$$P_i = \frac{F_{i,p}}{A_m \cdot \Delta p_i} \quad (4)$$

$$\alpha_{ij} = \frac{(y_i/y_j)_P}{(x_i/x_j)_F} \quad (5)$$

Where $P_i$=permeance of water molecule, mol/m²/s/Pa; $F_{i,p}$=permeate rate of water molecule across the membrane, mol/s; $A_m$=membrane area exposed to the feed, m²; $\Delta p_i$=partial pressure differential of water vapor across the membrane, Pa; $\alpha_{ij}$=separation factor of water to other molecule; $(y_i/y_j)_P$=ratio of molar fraction of water to other molecule in the permeate; $(x_i/x_j)_F$=ratio of molar fraction of water to other molecule in the feed 101.

Flux is often used as a simple way to characterize the membrane productivity and can be calculated from experimental measurements by the following equation:

$$J = \frac{Q_P}{A_m} \quad (6)$$

where J=flux, kg/m²/h; $Q_P$=permeate rate, kg/h; $A_m$=membrane area exposed to the feed, m².

Flux is not only affected by the membrane, but also affected by the feed composition, feed pressure, and permeate pressure. Generally, permeance is a better parameter to characterize the membrane performance.

For a given pressure gradient between the feed side 104 and permeate side 106, usage of the membrane area for removal of a certain amount of water decreases proportionally with increasing permeance. Thus, permeance has a direct impact on the membrane cost and device size. The separation factor affects energy efficiency. In general, energy efficiency increases with separation factor. The degree of the impact of the separation factor on energy efficiency depends on specific separation process purposes. For rough separation, such as concentration of ethanol in water from 55% to 90%, a relative low separation factor is sufficient. For a high degree of separation, such as concentrating ethanol in water from 90 to 99 wt. %, a much higher separation factor is needed.

Thin membrane sheets 102 are preferred to reduce volume and weight of the separation device and are also desired to obtain high membrane permeance. In an embodiment, the membrane sheet thickness is less than 200 μm, preferably less than 100 μm. The membrane sheet 102 should be mechanically strong and robust for being packaged into the device 100, for withstanding the pressure gradient under separation conditions, and for resisting thermal expansion stress during heating and cooling down. The membrane materials should be durable in the water-hydrocarbon under separation conditions. Molecular sieve materials such as zeolite are the preferred membrane materials. Excellent stability and selectivity of the $H_2O$-selective zeolite material has been demonstrated in oil, gas, and chemical processing as an adsorbent. However, the zeolite membrane typically cannot be made as self-supported thin sheets, meeting above device requirements. It is known that a high-performance zeolite membrane needs to be grown on a support. Growth of the zeolite membrane on porous ceramic supports has been demonstrated. The porous ceramic plates provide excellent chemical stability but are too fragile to be made as a thin, strong sheet. A porous polymeric sheet can be made thin but does not provide the desired chemical stability, thermal stability, and mechanical rigidity and strength for growing a high-performance zeolite membrane.

A preferred membrane sheet 102 according to an embodiment, is a water-selective molecular sieve layer 120 grown on a thin, porous metal-based support sheet 122. In an embodiment, the preferred molecular sieve material is a water-selective zeolite, such as LTA-type, Mordenite, MFI-type, and Faujasite-type zeolite. The zeolite layer thickness preferably is less than 20 μm, preferably less than 10 μm. The thin porous support sheet 122 preferably comprises sintered metallic grains with 3-dimensional networked pores. Preferably, the surface of the support sheet 122 is substantially free of pores above 5 μm for growing a high-performance zeolite membrane layer 120. The support sheet 122 preferably has a porosity about 30 to 70%, preferably 35 to 50% so that it preserves sufficient mechanical strength while not presenting significant transport resistance for permeated water vapor 118 to diffuse through. The zeolite membrane surface may be modified with other materials such as carbon and silicone to enhance its stability, but its crystal framework structure as measured by X-ray diffraction is preferably intact to assure the $H_2O$-molecular separation function.

The mini feed channels 114 may be formed by packing two membrane sheets 120 face-to-face. As a water-hydrocarbon mixture 101 is fed through the feed channels 114, water molecules transport from the bulk flow onto the membrane surface, get into the pores of the zeolite membrane layer 120, and diffuse across the membrane layer 120, while the other molecules in the mixture are rejected by the zeolite pores. The spacing between the two membrane sheets 102 is one design parameter and preferred in the range of 0.3 to 3.0 mm. The pressure drop of the feed flow through the feed channel 114 increases dramatically with decreasing the channel spacing. Thus, the channel spacing should not be too small for practical industrial application processes. On the other hand, the device volume and transport resistance of water molecule from bulk flow onto the membrane surface increase with channel spacing. Thus, the channel spacing should not be too large. To minimize the pressure drop and dead space, straight channels are preferred. The channel width and length can be sized for specific applications.

The feed mixture 101 in the feed channel 114 can be in liquid phase, vapor phase, or gas/liquid mixed phase. The feed pressure is preferably above atmospheric pressure. The pressure drop for the feed through the membrane channel is preferably less than 1 bar. The feed flows through the feed channel 114 is preferably above a predetermined LHSV or superficial velocity (U) to reduce the concentration polarization at the membrane surface. LHSV>10 l/h or U>10 cm/s is preferred.

The permeate channels 112 may be created by using a backing structure 110 in the back (permeate) side 106 of the membrane sheet 102. The backing structure 110 provides mechanical support for the membrane sheet 102 to withstand a pressure gradient between the feed side 104 and permeate side 106 under the separation conditions. The backing structure 110 also provides flow channels (permeate flow channels 112) for the permeated water vapor 118 to move out of the device. The backing structure 110 comprises permeate flow channels 112 having a hydraulic diameter in the range of 1 to 5 mm with an open frontal fraction of 0.4 to 0.9. The open frontal fraction is defined as ratio of the cross-sectional area for the permeate to flow to the total cross-sectional area. The hydraulic diameter should be large enough for the permeated water vapor to transport out of the membrane device without significant pressure drop. The hydraulic diameter should to be small enough to enhance the backing structure strength and reduce volume of the device. Straight permeate channels are preferred to reduce the pressure drop and to minimize the dead space. The backing structure 112 is preferably made of durable and strong materials, such as metals, alloys, and composites.

A cushion layer 108 may be placed between the backing structure 112 and the membrane sheet 102 to provide a smooth surface for the membrane sheet 102 to sit on and/or enhance structural integrity of the device 100. The cushion layer 108 preferably has porosity of 30 to 90% and thickness in the range of about 0 to about 0.5 mm.

The permeate side pressure can be the same as or similar to the feed side pressure if a sweep fluid is used to keep the partial pressure or chemical potential of water vapor 118 in the permeate side 106 less than the feed side 104 to drive the membrane separation. In a preferred embodiment, the permeate side 106 is pulled with vacuum to create a partial pressure gradient of water vapor across the membrane 102 with little or no usage of the sweep fluid. In an embodiment, the permeate side pressure may be less than 20 kPa while the feed side pressure is above 100 kPa. Water vapor diffusivity increases with decreasing pressure. Thus, water vapor diffusion rate across the membrane support 122 can be increased by operating the permeate side 106 under vacuum.

Figure 2A:
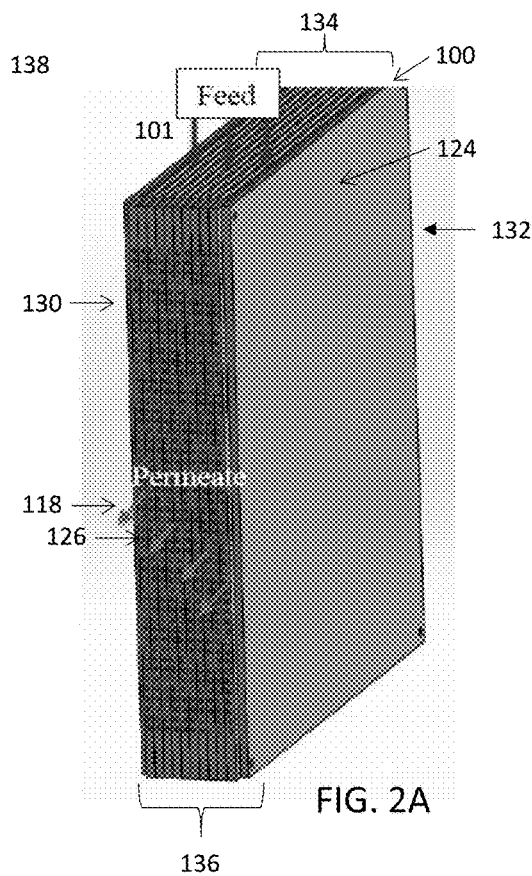
FIGS. 2A and 2B are perspective diagrams illustrating construction of cross-flow membrane modules with H$_2$O-selective membrane sheets including, 2A Frontal view of permeation slots and 2B Frontal view of feed flow channels according to an embodiment.
Figure 2B:
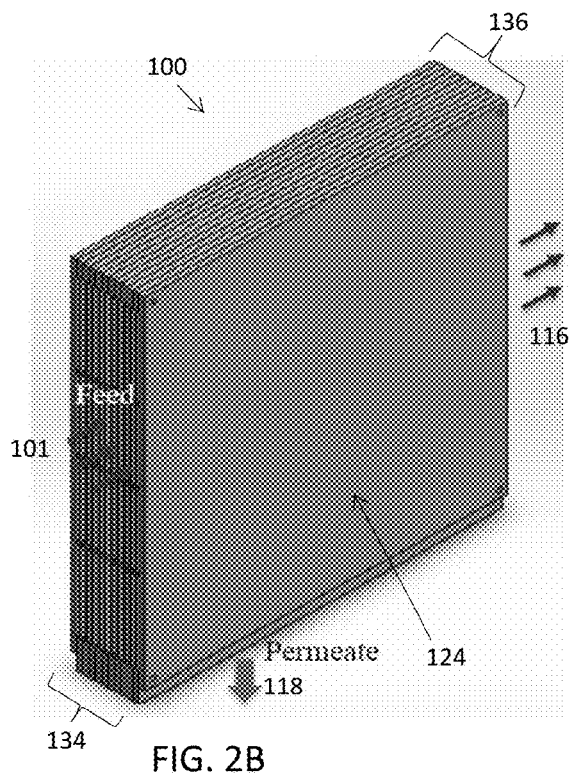

A number of the thin membrane sheets 102 can be packaged in a module 138 to generate an array of parallel feed channels 134 and another array of parallel permeate channels 136 in the separation device, as illustrated in FIGS. 2A and 2B. FIGS. 2A and 2B show a stack 100 of identical membrane sheets 102 to form two alternative arrays of feed and permeate channels 134, 136 in a perpendicular orientation. The stack 100 is sealed from exterior by use of two dense cover plates 124 on the two opposite ends. A front view of permeate outlet holes is shown FIG. 2A. The permeate holes are connected to the permeate channels 112 inside the stack 100. The permeate 118 could be drawn out of the stack interior from two opposite sides, i.e., front 130 and back 132 side in FIG. 2A. The front view of the feed channels 114 is shown in FIG. 2B. The feed 101 comes into the stack 10 from the front and out of the stack 100 from the back. Some spacers (not shown) may be placed between the membrane sheets 102 to reduce width of the feed channel 114 and prevent the membrane sheet 102 from damage by accidental pressure reverse. Under normal separation conditions, the feed side pressure is always greater than the permeate side so that the membrane sheet 102 is forced against the backing structure 110 inside the stack. The membrane sheet 102 could be popped up and broken if the permeate side pressure accidentally becomes greater than the feed. Such a problem can be mitigated by placing spacers between the membrane sheets 102.

Figure 3A:
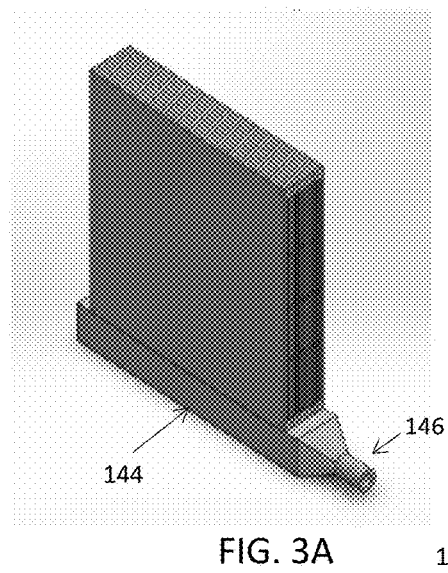
FIG. 3A is a perspective view of the manifold connection of a combination of a cassette stack with a permeate manifold according to an embodiment.
Figure 3B:
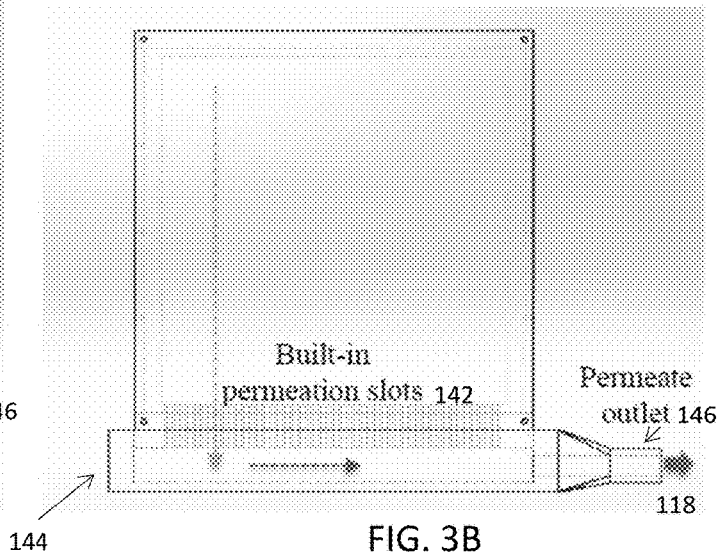
FIG. 3B is a schematic illustration of the cassette stack of FIG. 3A illustrating collection of the permeate according to an embodiment.

The permeated water vapor 118 coming out of these permeate holes 126 can be collected in a manifold 144 as illustrated in FIGS. 3A and 3B. The permeate side 130 of a membrane stack 100 can be inserted into a cavity 142 of the manifold 144 so that the permeated water vapor 118 is collected into one outlet 146 for tube connection.

Figure 4:
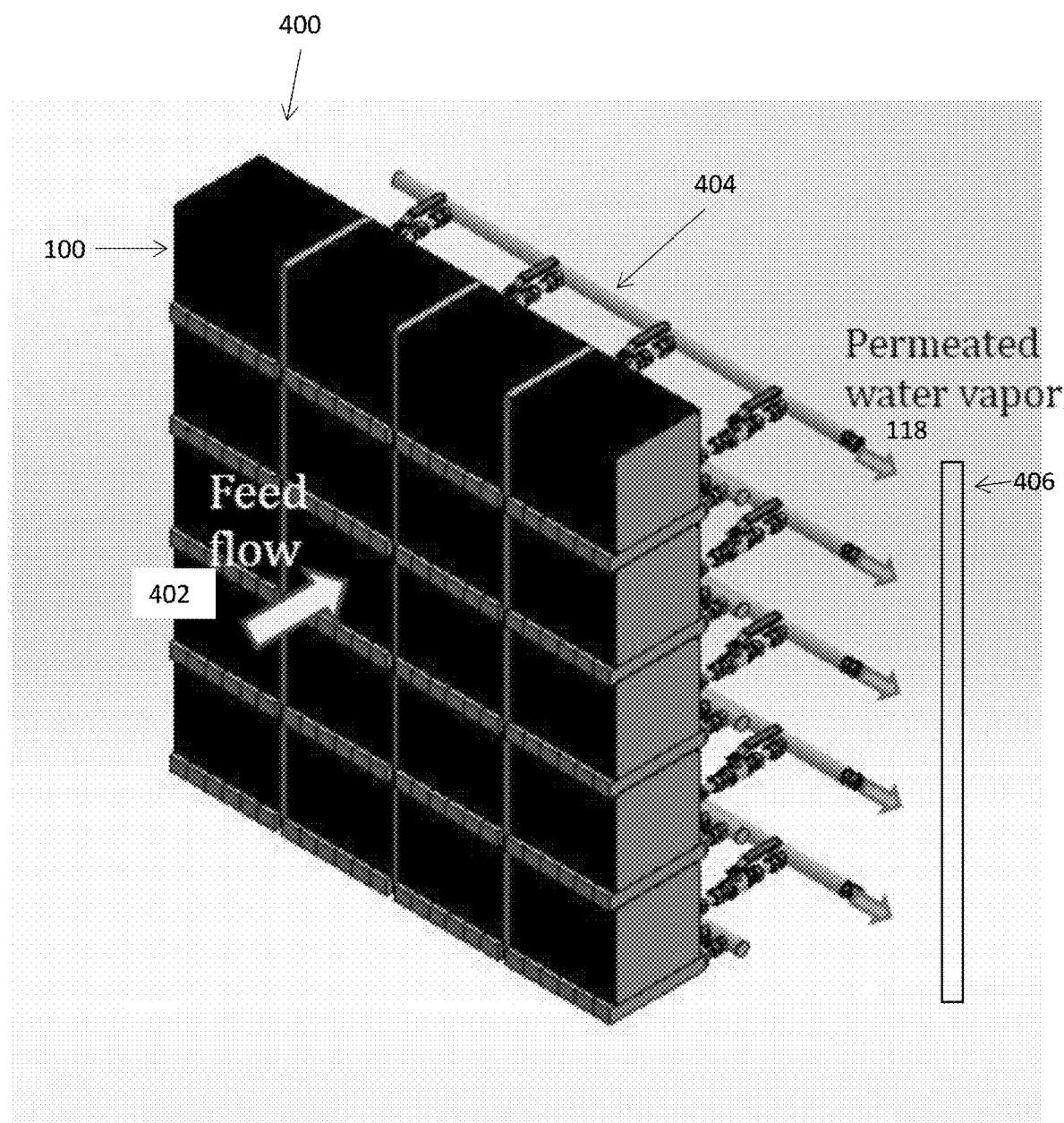
FIG. 4 is a perspective view of one section of membrane device comprising an array of module stacks in parallel according to an embodiment.

Many identical membrane stacks 100 can be assembled together to form one section 400 of the separation equipment. As illustrated in FIG. 4, one bulk feed flow 402 can flow through a section 400 comprising an array of the membrane stacks 100 arranged in parallel, while the permeated water vapor 118 from individual stacks 100 in one row is collected into one common duct 404. The water vapor permeate 118 from all the rows can be further collected to a larger common duct 406. Embodiments described herein solve the scale-up problem by combining a plurality of the identical membrane stacks 100 with a simple mechanical structure and configuration.

The width and height of a section 400 of packed membrane stacks 100 can be sized by use of the desired number of the stacks 100 according to specific application needs. Grouping of parallel membrane stacks 100 solves the scale-up problem regarding the desired cross-sectional flow area or processing flow rate capacity. For example, if one membrane stack 100 provides 400 $cm^2$ of the cross-sectional area for dewatering of 4 $m^3$/min vapor flow. In one embodiment, one hundred (100) of these membrane stacks 100 can be grouped in parallel to provide 40,000 $cm^2$ flow area for dewatering of 400 $m^3$/min vapor flow.

Figure 5A:
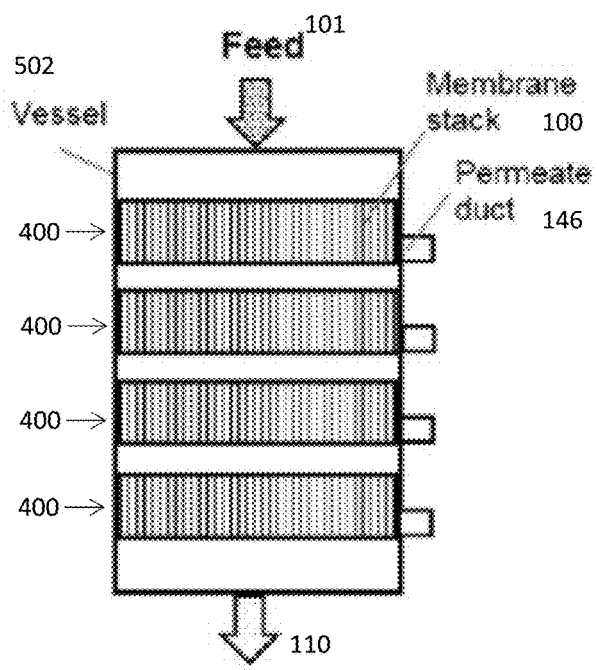
FIG. 5A is a schematic illustration of stage sections of a membrane separation device configured in series viewed along the feed flow direction according to an embodiment.
Figure 5B:
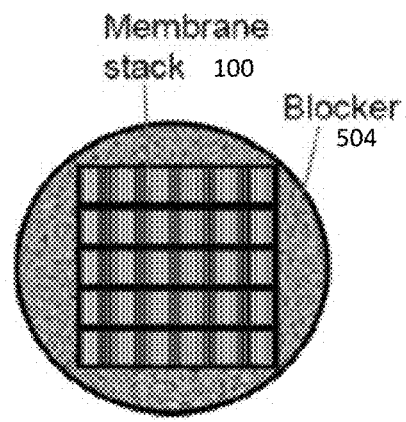
FIG. 5B is a cross-sectional view of the feed flow of the membrane separation device of FIG. 5A.

For fixed cross-sectional area of a membrane separation section, i.e., fixed number of the parallel membrane stacks 100, the targeted degree of dewatering at a given feed rate under given separation conditions can be obtained by use of a proper number of the separation stages. As illustrated in FIG. 5A, several membrane separation sections 400 can be staged in series. The permeate pressure for each section 400 can be controlled independently. Several separation sections 400 may be housed inside one vessel 502, such as a cylindrical vessel (FIG. 5B). The space between the vessel wall and boundary of the membrane stack can be blocked by use of some packaging materials 504 to prevent the feed flow from bypassing the membrane channels. For example, the above mentioned membrane stacks 100, if configured as a square, may be housed inside a cylindrical vessel 502 of about 300 cm inner diameter.

Figure 6:
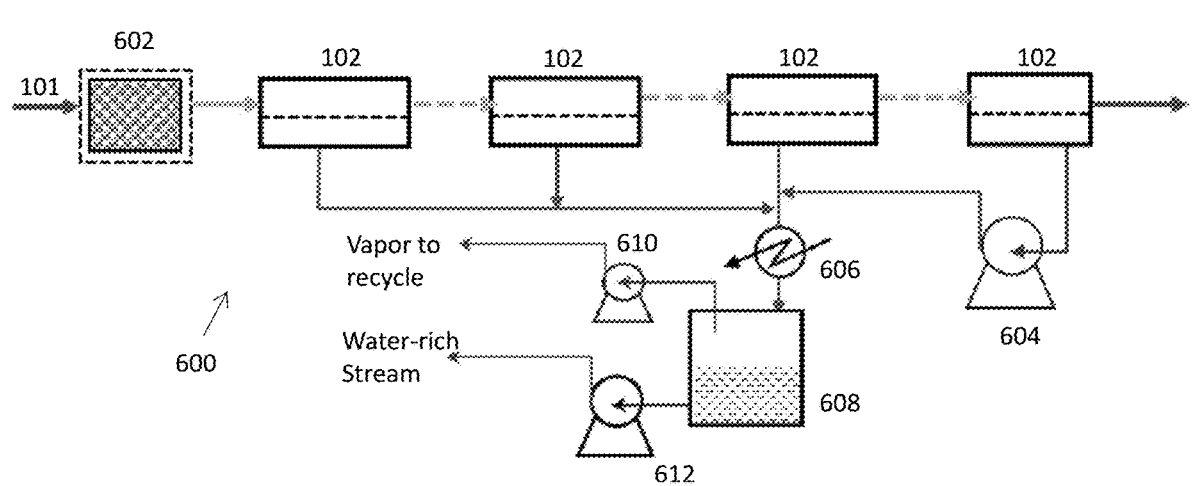
FIG. 6 is a flow diagram illustrating the dewatering process employing a mini-channel membrane device according to an embodiment.

A dewatering process/system 600 employing the membrane device is illustrated in FIG. 6. In the embodiment, $H_2O$-hydrocarbon mixtures contain certain impurities that could harm the membrane 102. The impurities can be scrubbed with a guard bed 602. For example, if water-ethanol feed contains some sulfuric acid impurity, the sulfuric acid can destroy the zeolite crystal structure if condensed on the membrane surface. The sulfuric acid impurity can be scrubbed with an alkaline-type sorbent such as CaO. The feed 101 flows into the membrane separation device 600 at pressure above atmospheric pressure as a hot fluid or vapor-phase fluid. Water in the feed 101 is removed through the membrane 102 as water vapor in the permeate side. The permeated water vapor 118 is cooled and condensed into liquid water under ambient temperature in a condenser 606. If the feed temperature is high and/or partial pressure of water vapor is high enough, sufficient vacuum may be created in the permeate side by cooling and condensing down the permeated water vapor 118 with typical industrial cooling water. The gas/liquid separator 608 is maintained under vacuum by pumping the non-condensed gas out of the separator with a vacuum pump 610. If the non-condensable contains significant fraction of hydrocarbons, it may be recycled to the membrane separator 102. If the water vapor pressure in the feed is low, which is the case for deep dewatering, a vacuum compressor 604 can be used to pull out the permeated water vapor 118 and maintain water vapor partial pressure in the permeate side such that it is lower than in the feed side. The compressed water vapor 118 can be cooled and condensed. The water can be removed with a water pump 612.

Example 1: Thin Membrane Sheet

Figure 7A:
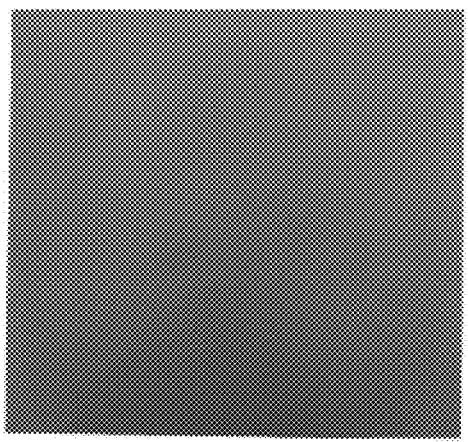
FIGS. 7A-7C are scanning electron microscope (SEM) micrographs of LTA-type zeolite membrane grown on a thin porous metal sheet support according to an embodiment.
Figure 7B:
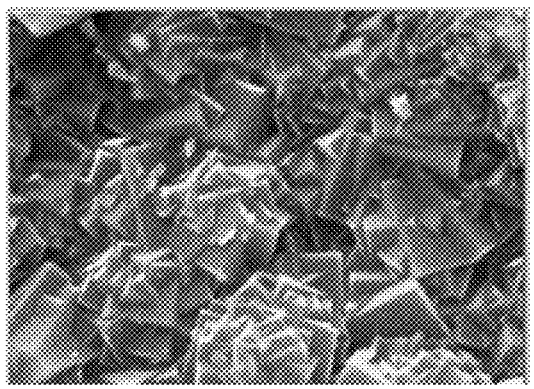
Figure 7C:
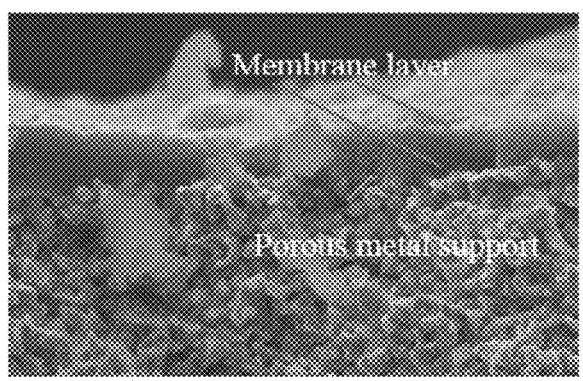

An embodiment of a thin membrane sheet 102 is illustrated in FIG. 7. A 20 cm×20 cm×55 μm zeolite membrane sheet (FIG. 7A) was prepared by growing NaA or LTA-type zeolite membrane on a 20 cm×20 cm×50 μm porous Ni alloy sheet, which has a surface pore size from 100 to 1000 nm as measured by Mercury porosimetry and 40% porosity. The membrane sheet is flat, strong enough to be self-supported, and is also flexible enough to be bent at radius greater than 2 cm. The membrane surface comprises inter-growth of zeolite crystals as shown by SEM image under 8000× magnification (FIG. 7B). No voids, pinholes, and cracks can be seen. Thus, only path for water molecule to move across the membrane is through the zeolite crystal in which well-defined pore structures are formed in the lattice frame. The zeolite membrane layer may be well adhered to the support sheet through a mechanical interlock mechanism (FIG. 7C, SEM image under 2000× magnification), i.e., some zeolite crystals grown into the support pores. FIG. 7C shows that the metallic grain sizes in the support are much larger than the zeolite crystal in the membrane layer.

Figure 8:
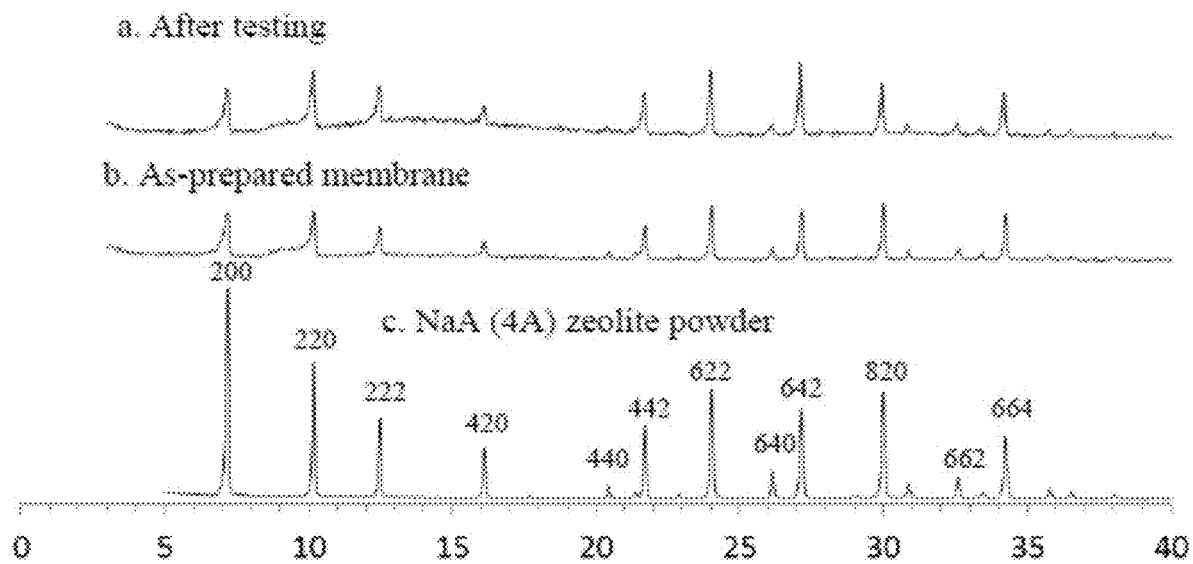
FIG. 8 is an x-ray diffraction (XRD) of a membrane grown on the thin porous metal sheet support according to an embodiment.

The lattice framework structure of the membrane layer can be determined by X-ray diffraction (XRD). FIG. 8 shows that the XRD pattern of as-grown zeolite membrane is the same as standard NaA zeolite powder. Absence of other strange peaks indicates the crystal phase purity of the zeolite membrane layer. The XRD pattern of the same membrane sheet after separation tests looks the same as the as-prepared one, which indicates stability of the zeolite membrane structure.

Figure 9:
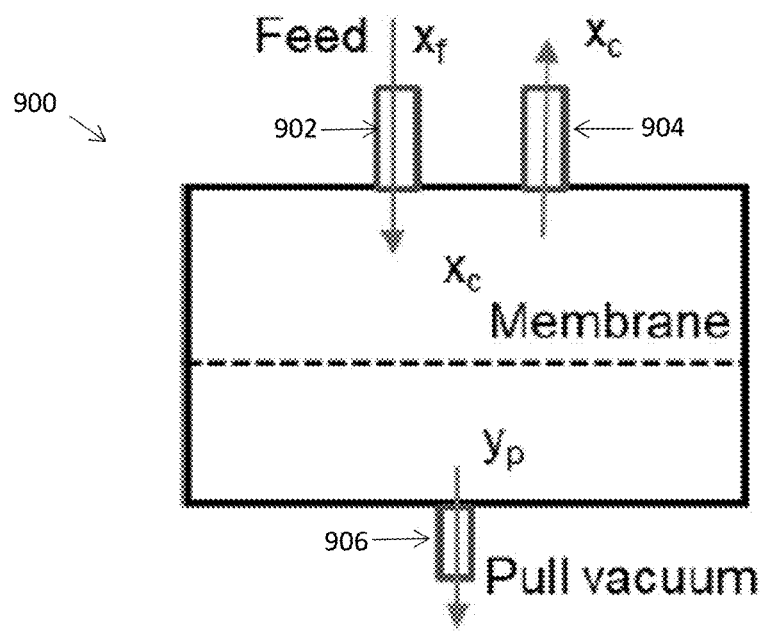
FIG. 9 is a schematic illustration of a differential membrane test cell according to an embodiment.

Example 2: Characteristics of the Thin Zeolite Membrane Sheet for Separation of Water-Hydrocarbon Mixtures Separation performance characteristics were tested by sampling 2.5-diameter coupons from a membrane sheet and loading them into differential membrane test cell 900 as illustrated in FIG. 9. In this test cell 900, the feed is provided via an inlet port 902 to the membrane surface and comes out at an exit port 904 adjacent to the injection point. Thus, the feed composition over the membrane surface is approximately the same. The water vapor is pulled out by vacuum via a vacuum port 906 and collected by condensation for analysis.

Characteristics of the membrane for separation of ethanol-water mixtures is shown in FIG. 10. With a feed of 10 wt. % water in ethanol, both water flux and water/ethanol separation factor increase with temperature. At 75° C., the water-ethanol feed under atmospheric testing pressure exists as vapor-liquid mixed phase. At 90° C. and 135° C., the feed is fully in vapor phase. The testing results indicate that the thin zeolite membrane sheet performs well regardless the state of phase of the feed. Increased water flux and separation factor at higher temperature can be explained by increased diffusion rate of water vapor through the zeolite pore, while the ethanol permeation is blocked by the membrane. At a constant temperature, FIG. 10 shows that water flux increases with water content in the feed, which can be explained by increased partial pressure of water vapor in the feed side. The $H_2O$/ethanol separation factor increases with decreasing water content, which suggests that the membrane is particularly selective for deep dewatering.

Figure 11:
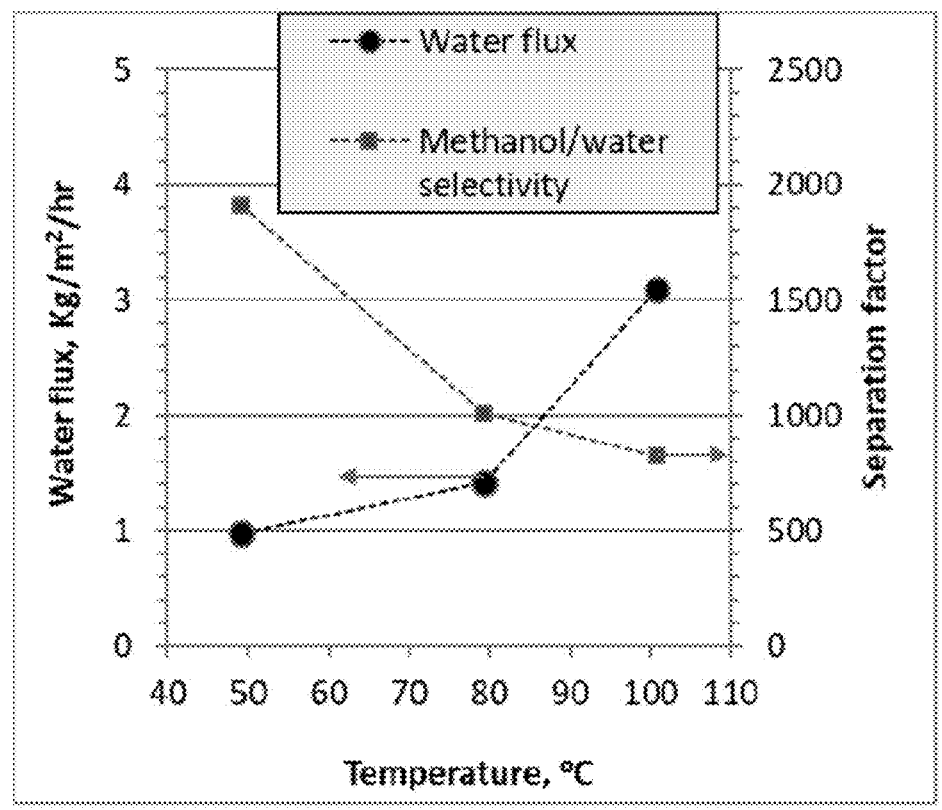
FIG. 11 is a plot illustrating the performance characteristics of a membrane for methanol-water separation (10 weight percent water in methanol, feed pressure equals 166 kPa, permeate pressure equals 1.1 kPa) according to an embodiment.

Separation performance of the thin NaA membrane for water-methanol mixtures is illustrated with a feed of 10 wt. % water in methanol. FIG. 11 shows that water flux increase with temperature as expected. Although $H_2O$/methanol separation factor decreases with temperature, the membrane remains highly selective toward $H_2O$ over methanol over the temperature range tested. The $H_2O$/methanol separation factor is greater than 800, which is sufficient for practical applications. The boiling point of methanol is 64.7° C., much lower than water. The high $H_2O$/methanol selectivity is attributed to $H_2O$-molecular specificity of the membrane.

Figure 12:
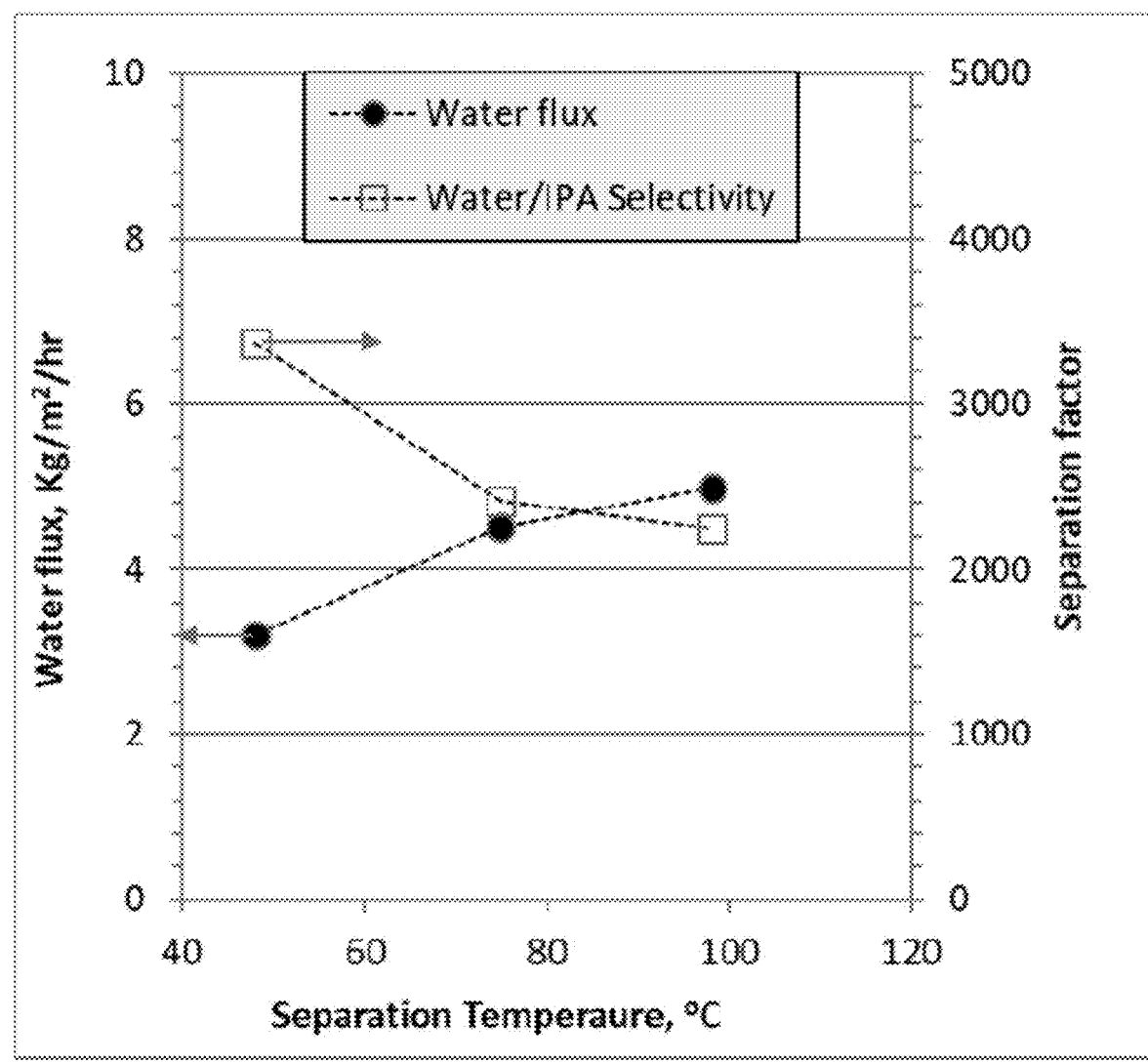
FIG. 12 is a plot illustrating the performance characteristics of a membrane for iso-propanol-water separation (10 weight percent water in iso-propanol, feed pressure equal 216 kPa, permeate pressure equals 1.4 kPa) according to an embodiment.
Figure 13:
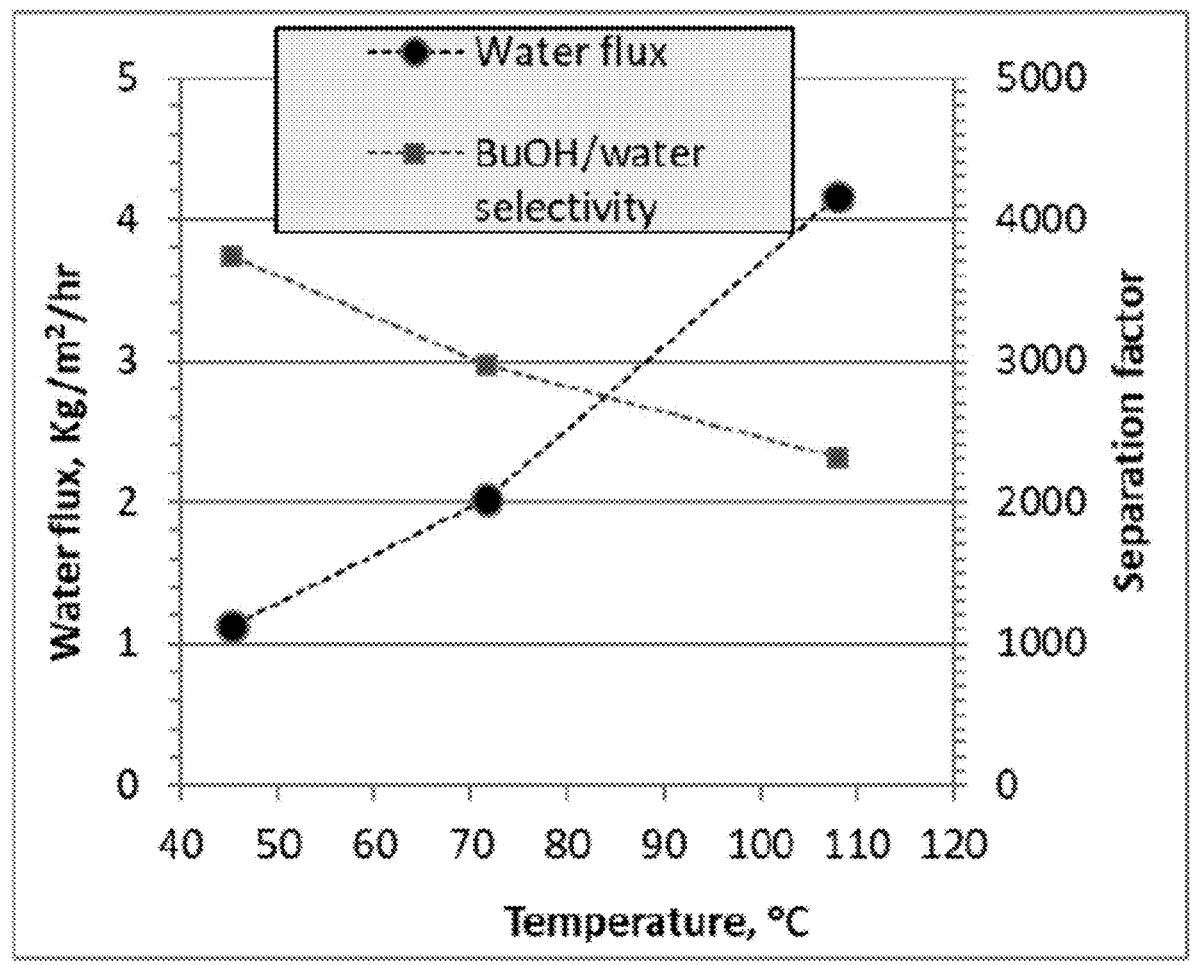
FIG. 13 is a plot illustrating the performance characteristics of a membrane for n-butanol-water separation (10 weight percent water in n-butanol, feed pressure equals 202 kPa, permeate pressure equals 2.1 kPa) according to an embodiment.

The $H_2O$-molecular specificity of the membrane is also shown for separation of water-isopropanol (FIG. 12) and water-butanol mixture (FIG. 13). FIG. 12 shows that for separation of 10 wt. % water in isopropanol, water flux increases with temperature and $H_2O$/isopropanol separation factor is above 2200 over the temperature range tested (48-98° C.). The feed is in liquid phase at 48° C. and in vapor phase at 98° C. The selective separation function of the membrane is not affected by the state of phase in the feed side.

Compared to separation of the water-isopropanol, water flux increases more rapidly with temperature for separation of a water-n-butanol mixture. The $H_2O$/n-butanol separation factor is above 2300 over the temperature range of 45 to 110° C.

$H_2O$-molecular specificity of the zeolite membrane 102 is clearly demonstrated by the testing results of those different water-alcohol mixtures. The high $H_2O$/alcohol selectivity is shown for all the mixtures over a broad range of temperature covering different phases in the feed from liquid, liquid-vapor, to vapor. The membrane is versatile for dewatering of various water-hydrocarbon mixtures. In general, water flux increases with temperature. Thus, the separation is preferably conducted at high temperatures to reduce membrane usage.

Example 3: Separation of Ethanol-Water in a Mini-Channel Separator

Separation performance characteristics of the thin zeolite membrane sheet in a mini-channel was tested on a simple, single-sheet test cell. As illustrated in FIG. 14, a 3.5 cm×5.0 cm membrane sheet was loaded into a rectangle test cell 1400 to obtain one feed channel of 20 mm width×0.5 mm height×40 mm length, while five of 3.2 mm width×1.0 mm height×40 mm length channels were evenly distributed on the permeate side. The feed was introduced from one end of the channel via an inlet port 902 and discharged at the opposite end via an exit port 904. The permeate side was pulled under vacuum via vacuum port 906. Under steady-state separation conditions, the feed and raffinate were sampled and analyzed to determine water removal. The permeate was condensed, collected, and analyzed to calculate flux and separation factor.

FIG. 15A shows water flux and water content in the permeate at different LHSV. With a constant feed of 10 wt. % water in ethanol, water content in the permeate was above 95 wt. % for all the samples analyzed. Water flux slightly increased with LHSV and reached a plateau of about 4 kg/m²/h. The $H_2O$ permeance was calculated by use of an average partial pressure differential of water vapor between the feed and permeate and was in the range of 1.4 to 2.4E-6 mol/(m²·s·Pa) over the range of LHSV tested. No significant impact of LHSV on the permeance was observed, which suggests that $H_2O$ mass transfer from bulk onto the membrane surface in the feed channel may not be a limiting factor with the 0.5 mm channel. FIG. 15B shows that almost 99% of water was removed at low LHSV with only 40 mm-long membrane and water removal decreased with LHSV.

The separation performance with constant feed conditions was tested at different permeate pressures. Water flux rapidly decreased with increasing permeate pressure (FIG. 16a). Water content in the permeate was 99% for all the samples collected, indicating excellent $H_2O$/ethanol selectivity. Further, $H_2O$ permeance decreased with increasing permeate pressure (FIG. 16B). If water flux was only affected by partial pressure differential, $H_2O$ permeance should be approximately constant. The fact that $H_2O$ permeance decreased with increasing permeate pressure indicates that $H_2O$ diffusion rate in the permeate side could play a role in determining water flux, because diffusivity increases proportionally with decreasing pressure. As a result, % water removal decreased with increasing permeate pressure (FIG. 16B).

Under constant LHSV and permeate pressure, FIG. 17A shows that water flux rapidly increases with water content in the feed, which is attributed to increased water vapor partial pressure in the feed. $H_2O$ permeance slightly decreased with increasing water content in the feed (FIG. 17B), suggesting that the partial pressure of water vapor in the feed does not have a linear impact on water flux. The % of water removal decreased with increasing water content in the feed (FIG. 17B) as expected.

Under constant feed composition, LHSV and temperature, a trend of water flux decrease with increasing feed pressure is shown in FIG. 18A. At high feed pressure, water content in the permeate decreased, suggesting decreased $H_2O$/ethanol selectivity. FIG. 18B shows trends of $H_2O$ permeance and % water removal decrease with increasing feed pressure. Large degree of data fluctuation in this batch of experimental measurements was likely caused by an unstable flow pattern in the feed channel. At 89° C. constant temperature, the fraction of the liquid phase in the feed channel increases with feed pressure. Different from the differential test cell, the feed composition varied along the membrane length, which could result in un-stable gas/liquid two-phase flow patterns. Unless the feed is fully in vapor phase, increasing feed pressure may not have positive impacts on % de-watering and $H_2O$/ethanol selectivity.

Separation temperature is a process parameter. The mini-channel separation performances at different temperatures are shown in FIGS. 19A and 19B. As the temperature was raised from 80 to 120° C., water flux tended to increase with temperature (FIG. 19A). However, water flux decreased with further increasing temperature. This can be explained by reduced adsorption of water into the zeolite pore at higher temperatures. The membrane showed excellent $H_2O$/ethanol selectivity over the broad range of temperature tested (80-200° C.). Water content in the permeate was all above 95 wt. % with a 10 wt. % feed. Significant water removal was achieved over the temperature range (FIG. 19B). $H_2O$ permeance was not significantly affected by the temperature.

These parametric testing results confirm that the mini-channel membrane separation comprising the thin zeolite membrane sheet is effective for separation of water-ethanol or water-hydrocarbon mixtures in general over a wide range of process conditions.

Example 4: Assembly of Thin Zeolite Membrane Sheets into Mini-Channel Membrane Separator Fabrication of a mini-channel membrane separator is illustrated with 20 cm×20 cm×55 μm of the NaA/porous Ni sheet. First, two membrane sheets are fixed onto a cassette frame 140 (FIG. 20A) with the zeolite membrane surface exposed to the outside to form a cassette 138. The cassette frame 140 provides a 19 cm×19 cm cavity and 5 mm wide regress around the cavity for adhesion of the membrane sheet. A 19 cm×19 cm corrugated stainless steel sheet with waved permeate channels was placed inside the cavity 142 as the backing structure 110. The wavelength and amplitude of the permeate channels 112 are 1.5 mm and 3.0 mm, respectively. A 19 cm×19 cm×0.25 mm of polyester cloth was used as a cushion between the backing structure 110 and the membrane sheet 102. The front and back edges of the cassette frame 140 have a thickness of 3.4 mm, while thicknesses on the top and bottom edge are 2.0 mm. Fifty (50) 1 mm high×2 mm wide permeation holes 141 were made on the front edge and connected with the permeate channels 112 inside the frame cavity.

Eleven (11) of the membrane cassettes 138 were bonded together to form a membrane stack 100 (FIG. 20B). Two cover plates 124 were attached to the two ends of the stack. Then, the edge having permeation holes 141 was inserted into a manifold 144 to form a working unit 100 (FIG. 3A). The water-hydrocarbon mixture can be fed into the mini-channels formed between the membrane cassettes 138. The feed channel 114 sizes are 1.4 mm height×50 mm width×230 mm length. The resulting module dimensions are 48 mm width×260 mm height×230 mm depth. The unit has 0.8 $m^2$ of active membrane working area, which corresponds to a membrane area packing density of 280 $m^2$ per $m^3$ of the module volume.

Example 5: Application of the Membrane Separator to Dewatering of Industrial Ethanol Fuel Production For large-scale industrial applications, the mini-channel membrane stacks 100 can be grouped into one section of 160 $m^2$ working area. The major design parameters according to an embodiment are listed in Table 2. In total, 40,000 thin membrane sheets with 20 cm×20 cm active working area are used. 100 of these membrane sheets can be first packaged into a membrane stack of 4 $m^2$ membrane area. Then, 40 of the membrane stacks 100 may be configured together in parallel to form one membrane separation section 400. The section provides 1.44 m×1.50 m cross-sectional area for feed flow. The section depth is 0.24 m. These membrane sections 400 can be staged in series for dewatering of water ethanol in ethanol fuel production plants.

FIG. 21A shows the major process steps for production of ethanol fuel from corn feedstock in a conventional process. The clarified fermentation broth contains about 12 wt. % ethanol and is first enriched to about 58 wt. % through fractionation—for example, a beer column. Then, the ethanol content is increased by about 93 wt. % by distillation. The remaining water is removed by adsorption to produce>99 wt. % ethanol. The membrane device can be used to replace distillation column to produce about 97 wt. % ethanol (FIG. 21B). The residual water can be removed by adsorption. Overhead vapor from the fractionation column can be fed into the membrane separation device to conduct vapor-phase separation over a temperature range 90-130° C. and no additional heat input is needed. The membrane device can also be used to replace both distillation and adsorption by operating separation at high degree of dewatering (FIG. 21C).

FIGS. 22A and 22B show variations of water molar fraction in product stream with membrane separation stage for dewatering of 40 million gallon per year corn ethanol plants in two process schemes depicted in FIGS. 21B and 21C, respectively. 10 of the 160 $m^2$ membrane section as described in Table 2 are staged in series. The permeate pressure in each stage may be adjusted independently. FIG. 22A shows that water molar fraction in the product stream can be affected by using different permeate pressures. But, the number of separation stages has more impact on water removal. With 10 stages of the 160 $m^2$ membrane section, the water molar fraction can be reduced from 65% in feed to 16% in the product (=93 wt. % ethanol) with both permeate pressure profiles plotted in FIG. 22A. To produce>99 wt. % ethanol, two trains of the 10-stage membrane separation are needed. As shown in FIG. 22B, water molar fraction can be reduced from 65% in feed to about 1% (99 wt. % ethanol) with either of the two permeate pressure profiles simulated. However, to obtain higher degree of de-watering (>99 wt. % ethanol), the permeate pressure in last stage must be sufficiently low (e.g., <1 kPa).

The membrane area usage may be doubled to replace both distillation and adsorption. The membrane separation device provides great flexibility for installation and operation. The number of membrane separation stages and degree of water removal can be optimized based on specific plant configuration. For example, replacement of distillation may be used for retrofitting of existing plants that already have adsorption units, and complete membrane separation may be used to build new plants.

TABLE 2

| Sizing of one-section membrane separator at industrial scale | |
|---|---|
| Membrane area for one section, $m^2$ | 160 |
| Thin membrane sheet of working size | 0.020 |
| Width, m | 0.200 |
| Length, m | 0.200 |
| Working area of each sheet, $m^2$ | 0.040 |
| No of membrane sheet required | 40,000 |

TABLE 2-continued

Sizing of one-section membrane separator at industrial scale

| Membrane stack | |
| --- | --- |
| Feed channel height - spacing between the membrane surfaces, m | 1.40E−03 |
| Cassette thickness - spacing between the back surfaces of the membrane sheet, m | 2.00E−03 |
| Width of cassette frame edges, m | 2.00E−03 |
| Cover plate thickness, m | 5.00E−03 |
| No of membrane sheets in one stack | 100 |
| Membrane area/stack, m$^2$ | 4.0 |
| Stack thickness, m | 0.180 |
| Manifold height, m | 0.05 |
| Section size | |
| No of membrane stacks in a row | 8 |
| No of rows | 5.0 |
| No of membrane stacks/section | 40 |
| Overall width, m | 1.44 |
| Overall height, m | 1.50 |
| Overall depth, m | 0.24 |

While a number of embodiments of the present invention have been shown and described, it will be apparent to those skilled in the art that many changes and modifications may be made without departing from the invention in its broader aspects. The appended claims, therefore, are intended to cover all such changes and modifications as they fall within the true spirit and scope of the invention.

RELEVANT PRIOR ART

The references listed below are hereby incorporated by reference in their entirety.
1. S. Wee, C. Tye, S. Bhatia "Membrane separation process-pervaporation through zeolite membrane" Sep. Purif. Technol., 63 (2008) 500. Various membranes were reviewed for pervaporation separation of water-alcohols.
2. Y. Morigami, M. Kondo, J. Abe, H. Kita, and K. Okamoto. "The first large-scale pervaporation plant using tubular-type module with zeolite NaA membrane" Sep. Purif. Technol. 25 (2001) 251. Commercial tests of ceramic tube-supported zeolite membranes for dewatering of ethanol were reported and the zeolite membrane showed much higher flux and selectivity than the other membrane materials.
3. W. Liu, J. Zhang, N. Canfield, L. Saraf "Preparation of Robust, Thin Zeolite Membrane Sheet for Molecular Separation" Ind. Eng. Chem. Res., 50 (20) (2011)11677-11689. Different preparation methods were studied to grow zeolite membranes on the thin porous metal sheet support.
4. Augustin et al. Desalination 146 (2002) 23-28. The zeolite membrane was prepared on sintered porous metal plate or metallic mesh with thickness~1 mm, a wide range of pore sizes (0.2 to 40 μm).
5. J. R. Kwiatowski, A. J. McAloon, F. Taylor, D. Johnston "Modeling the process and costs of fuel ethanol production by the core dry-grind process" Ind. Crop. Prod. 23 (2006) 288. Typical ethanol production process for core ethanol plants was described.
6. Pierre Plante, Bruno de Caumia, Christian Roy, Gaetan Noel. "Ethanol Processing with vapor Separation Membranes" US20080207959A1 (Assignee: Parker Filtration BV; Original Assignee: Vaperma Inc.; Priority date 2007-02-28). A process for removing water from a mixture comprising ethanol and water, the process comprising steps of a) distilling the mixture to produce distillate; b) feeding at least a portion of the distillate to a gas separation membrane; c) collecting permeate from the gas separation membrane; and, d) compressing at least some of the permeate and using heat carried by the permeate to assist in distilling the mixture.
7. Armin Rix, Frank Eloper, Jochen Praefke, Wilfried Büschken. "Process for dewatering ethanol" U.S. Pat. No. 7,399,892B2 (Current Assignee: Evonik Oxeno GmbH; Original Assignee: Oxeno Olefinchemie GmbH; Priority date: 2006 Jan. 25). A process for preparing relatively low-water ethanol from at least two streams of relatively water-rich ethanol that have a different water content, the process comprising introducing separately the ethanol streams with different water contents into different membrane units in which the ethanol streams are each separated into relatively low-water ethanol as the retentate and relatively water-rich permeate, and combining the retentate stream from at least one membrane unit for separating an ethanol stream with a relatively high water content with the feed stream and/or the retentate stream of at least one other membrane unit for separating an ethanol stream, wherein only streams that have a difference in ethanol concentration of not more than 1% by mass absolute are combined.
8. Anurag P. Mairal, Alvin Ng, Richard W. Baker, Ivy Huang, Jennifer Ly "Ethanol Recovery Process" U.S. Pat. No. 7,399,892B2 (Assignee: Membrane Technology and Research Inc., Menlo Park, Calif.; Date of patent: Jun. 8, 2010). The claimed process consisting of several major process steps in which several sub-process steps are involved.

I claim:
1. A device for separation of water-hydrocarbon mixtures comprising:
   i) $H_2O$-selective membrane sheets having a thickness less than 1 mm, $H_2O$ permeance greater than $1 \times 10^{-6}$ mol/$(m_2 \cdot Pa \cdot s)$ and $H_2O$/hydrocarbon separation factor greater than 2;
   ii) feed channels having a hydraulic diameter in the range of 0.5 to 5.0 mm for the water-hydrocarbon mixtures to flow over the $H_2O$-selective membrane surface at pressure drop less than 100 kPa; and
   iii) a backing structure for supporting the back side of at least one of the membrane sheets and providing permeate channels of hydraulic diameter of 0.5 to 5.0 mm for removal of the permeated water vapor out of the device at a pressure drop less than 20 kPa.
2. The device of claim 1, wherein at least one of the membrane sheets is a $H_2O$-selective molecular sieve membrane with a thickness less than 20 μm grown on a porous metal-based support sheet of thickness less than 200 μm, a porosity from 25 to 70%, and substantially free of pores greater than 5 μm on a surface where the membrane grows.
3. The device of claim 2, wherein the molecular sieve membrane has a zeolite crystal phase of LTA-type, Mordenite-type, MFI-type or Faujasite-type lattice framework.
4. The device of claim 1, further comprising a cushion, wherein the backing structure is in contact with at least one of the membrane sheets through the cushion, wherein the cushion has a of porosity from 30 to 90%, a thickness from 0 to 0.5 mm, and substantially free of any protrusions or outward sharp features with height greater than at least one of the membrane sheet thicknesses.
5. The device of claim 1, wherein the feed channels comprise an array of parallel straight channels.
6. The device of claim 1, wherein the permeate channels comprise an array of parallel straight channels.

7. A water removal process comprising:
i) introducing a water-hydrocarbon mixture into feed channels having a hydraulic diameter in a range of 0.5 to 5.0 mm at an inlet pressure, flowing the water-hydrocarbon mixture over a surface of a thin $H_2O$-selective membrane sheet having a thickness less than 1 mm, $H_2O$ permeance greater than $1\times10^{-6}$ mol/($m^2\cdot Pa\cdot s$) and a $H_2O$/hydrocarbon separation factor greater than 2, and removing the water-hydrocarbon mixture from the feed channel at an outlet pressure;
ii) transporting water molecules across the membrane sheet and removing the water molecules from an opposite side of the membrane sheet, the water molecules in a vapor-phase at a permeate pressure; and
iii) removing the permeated water vapor through a backing structure having permeate channels having a hydraulic diameter of 0.5 to 5.0 mm.

8. The method of claim 7, wherein the thin membrane sheet is a $H_2O$-selective molecular sieve membrane having a thickness less than 20 μm and grown on a porous metal-based support sheet having a thickness less than 200 μm, a porosity from 25 to 70%, and substantially free of pores greater than 5 μm on the surface where the membrane is grown.

9. The method of claim 8, wherein the membrane sheet is a molecular sieve membrane and comprises a zeolite crystal phase of LTA-type, Mordenite-type, MFI-type or Faujasite-type lattice framework.

10. The method of claim 7, wherein the backing structure is in contact with the membrane sheet through a cushion having a porosity from 30 to 90%, a thickness from 0 to 0.5 mm, and free of any protrusions or outward sharp features with height greater than the membrane sheet thickness.

11. The method of claim 7, wherein the water-hydrocarbon mixture is a water-alcohol or water-ethanol mixture.

12. The method of claim 7, wherein the water-hydrocarbon mixture is in a vapor phase.

13. The method of claim 7, wherein the inlet and outlet pressures of the feed channels are above 100 kPa.

14. The method of claim 7, wherein the permeate pressure is below 20 kPa.

15. The method of claim 7, wherein the water-hydrocarbon mixture flows in the feed channels at a superficial linear velocity greater than 10 cm/s.

16. The method of claim 7, wherein the feed channels comprise an array of parallel, straight channels.

17. The method of claim 7, wherein the permeate channels comprise an array of parallel, straight channels.

* * * * *